(12) United States Patent
Deck et al.

(10) Patent No.: US 11,678,824 B2
(45) Date of Patent: Jun. 20, 2023

(54) SENSOR ASSEMBLY AND METHOD FOR DETECTING AT LEAST ONE ANALYTE IN A BODY FLUID

(71) Applicant: Roche Diabetes Care, Inc., Indianapolis, IN (US)

(72) Inventors: Frank Deck, Niederkirchen (DE); Joachim Jager, Bruchsal (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 970 days.

(21) Appl. No.: 15/775,042

(22) PCT Filed: Jan. 19, 2017

(86) PCT No.: PCT/EP2017/051095
§ 371 (c)(1),
(2) Date: May 10, 2018

(87) PCT Pub. No.: WO2017/125500
PCT Pub. Date: Jul. 27, 2017

(65) Prior Publication Data
US 2018/0271414 A1    Sep. 27, 2018

(30) Foreign Application Priority Data
Jan. 19, 2016 (EP) .................................. 16151936

(51) Int. Cl.
*A61B 5/1473* (2006.01)
*A61B 5/00* (2006.01)
*H01R 13/625* (2006.01)

(52) U.S. Cl.
CPC .......... *A61B 5/1473* (2013.01); *A61B 5/6833* (2013.01); *A61B 5/6847* (2013.01);
(Continued)

(58) Field of Classification Search
None
See application file for complete search history.

(56) References Cited

U.S. PATENT DOCUMENTS 5,413,690 A    5/1995  Kost
5,762,770 A    6/1998  Pritchard et al.
(Continued)

FOREIGN PATENT DOCUMENTS

CN    101393198       3/2009
EP    0 801 927 A    10/1997
(Continued)

OTHER PUBLICATIONS

Office Action and Search Report in related CN201780007193.5 dated Jun. 16, 2020.
(Continued)

*Primary Examiner* — Michael R Bloch
(74) *Attorney, Agent, or Firm* — Woodard, Emhardt, Henry, Reeves & Wagner, LLP

(57) ABSTRACT

A sensor assembly (226) for detecting at least one analyte in a body fluid, a sensor patch (134) for use in a sensor assembly (226), an electronics unit (188) for use in a sensor assembly (226) and a method for producing a sensor assembly (226) are disclosed. The sensor assembly (226) comprises:
 at least one sensor patch (134), having
  at least one body mount (136) configured for attachment to a body of a user; and
(Continued)

at least one sensor (110) for detecting the at least one analyte in the body fluid, the sensor (110) having at least two electrodes (114) configured for detecting the analyte, the sensor (110) further having at least two sensor contacts (116) for electrically contacting the electrodes (114);

wherein the sensor patch (134) comprises a patch housing (138) with a patch bayonet contour (140);

at least one electronics unit (188) attachable to the body mount (136), having at least one electronics component (200) for one or more of controlling the detection of the analyte or transmitting measurement data to another component, wherein the electronics unit (188) further comprises an electronics unit housing (202) having an electronics unit bayonet contour (204);

wherein the patch bayonet contour (140) and the electronics unit bayonet contour (204) in conjunction form a bayonet connector (228) configured for establishing a releasable mechanical connection between the electronics unit (188) and the sensor patch (134).

17 Claims, 8 Drawing Sheets

(52) U.S. Cl.
CPC ......... *A61B 5/6849* (2013.01); *H01R 13/625* (2013.01); *A61B 2560/045* (2013.01); *A61B 2562/02* (2013.01); *A61B 2562/125* (2013.01); *A61B 2562/227* (2013.01); *H01R 2201/12* (2013.01)

(56) References Cited

U.S. PATENT DOCUMENTS

| | | | |
|---|---|---|---|
| 5,798,031 | A | 8/1998 | Charlton et al. |
| 5,879,373 | A * | 3/1999 | Roper ................ A61B 5/14552 600/344 |
| 6,129,823 | A | 10/2000 | Hughes et al. |
| 6,360,888 | B1 | 3/2002 | McIvor et al. |
| 2005/0013731 | A1 | 1/2005 | Burke et al. |
| 2006/0068625 | A1 | 3/2006 | Kim et al. |
| 2008/0009167 | A1 | 1/2008 | Hillis et al. |
| 2008/0242962 | A1 | 10/2008 | Roesicke et al. |
| 2011/0172508 | A1 | 7/2011 | Chickering et al. |
| 2012/0078071 | A1 | 3/2012 | Bohm et al. |
| 2012/0143135 | A1 * | 6/2012 | Cole .................... A61M 5/158 604/164.04 |
| 2013/0267809 | A1 * | 10/2013 | Brister ............... A61B 5/14503 600/347 |

FOREIGN PATENT DOCUMENTS

| | | |
|---|---|---|
| EP | 1 971 263 A2 | 9/2008 |
| EP | 2 721 996 | 7/2015 |
| EP | 2 532 302 | 11/2015 |
| WO | WO 2007/071562 | 6/2007 |
| WO | WO 2011/044386 | 4/2011 |

OTHER PUBLICATIONS

International Application PCT/EP2017/051095 Ioternational Search Report and Written Opinion, dated Apr. 3, 2017.

* cited by examiner

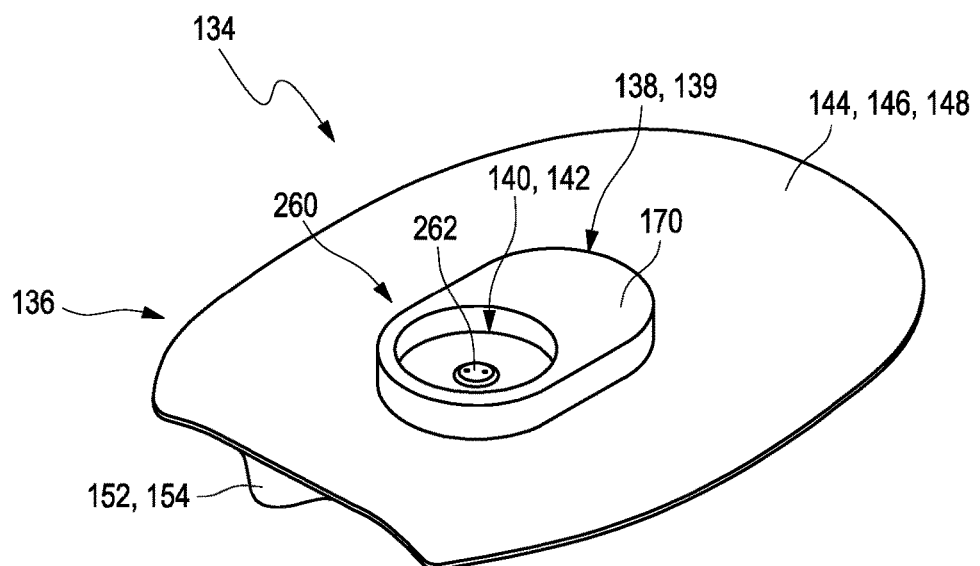
Fig. 7
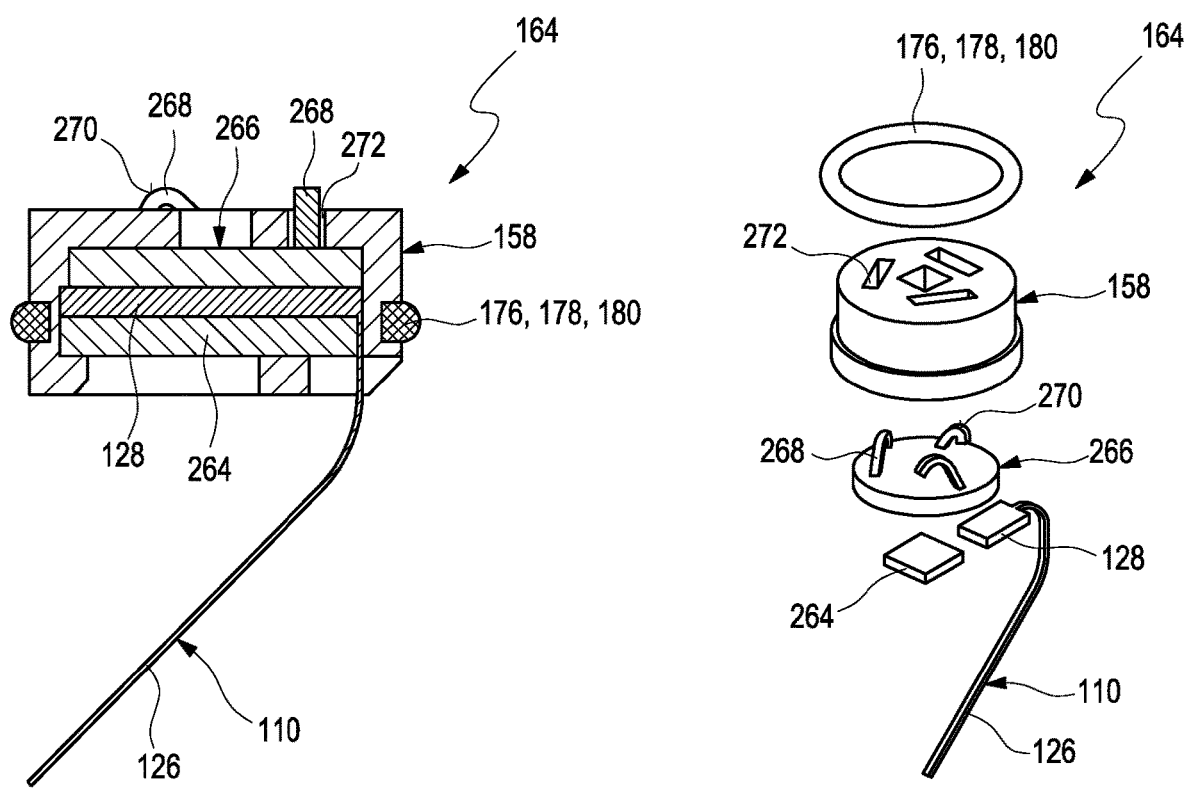
Fig. 8 A                                    Fig. 8 B

SENSOR ASSEMBLY AND METHOD FOR DETECTING AT LEAST ONE ANALYTE IN A BODY FLUID

FIELD OF THE INVENTION

The invention relates to a sensor assembly for detecting at least one analyte in a body fluid as well as to a sensor patch assembly and an electronics unit for use in the sensor assembly. The invention further relates to a method for producing a sensor assembly for detecting at least one analyte in a body fluid. The devices and methods according to the present invention may mainly be used for long-term monitoring of an analyte concentration in a body fluid, such as for long-term monitoring of a blood glucose level or of the concentration of one or more other types of analytes in a body fluid. The invention may both be applied in the field of home care and in the field of professional care, such as in hospitals. Other applications are feasible.

RELATED ART

Monitoring certain body functions, more particularly monitoring one or more concentrations of certain analytes, plays an important role in the prevention and treatment of various diseases. Without restricting further possible applications, the invention will be described in the following text with reference to blood-glucose monitoring. However, additionally or alternatively, the invention can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems typically are transcutaneous systems or subcutaneous systems, wherein both expressions, in the following, will be used equivalently. This means that the actual sensor or at least a measuring portion of the sensor is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically further also acts as a protection against humidity and other detrimental substances and, as an example, may comprise one or more cover layers such as resists.

As outlined above, in transcutaneous systems, a control part is typically required, often also referred to as an electronics unit or a transmitter, which may be located outside the body tissue and which has to be in communication with the sensor. Typically, this communication is established by providing at least one electrical contact between the sensor and the control part, which may be a permanent electrical contact or a releasable electrical contact.

EP 2 721 996 A1 discloses a medical device kit comprising a medical instrument with a first connector, the first connector comprising at least one first electrical connection and a sealing cavity at least partially surrounding the at least one first electrical connection. The sealing cavity comprises a sealing surface and a wedging surface. The medical device kit further comprises a sealing cap, comprising a sealing tube with an inner cavity. The sealing tube has a flexible tip region. The wedging surface is operable for forcing the flexible tip against the sealing surface to form a flexible tip seal that seals the at least one first electrical connection within the sealing tube.

WO 2011/044386 A1 discloses an inserter subassembly that is engaged by turning a rotatable trigger to implant an analyte sensor. Therein, a sensor system is described that has a mount including a seal fixture configured to protect a sensor disposed on the mount body. The seal fixture includes first and second legs to attach to the mount. The seal fixture further includes a circular body to cover the sensor while positioned on the mount. The circular body is attached to first and second legs. The seal fixture pivots upwardly and downwardly. In this manner, when sensor is disposed on the upper surface of mount, the circular body of seal fixture covers the sensor, and in particular, the sensor electric terminals or contacts. The pivoting action enables the seal fixture to provide the inserter with access to mount for insertion of sensor. Additionally, the seal fixture allows the sensor to be pressed flat to the mount, i.e. disposed in a horizontal orientation with respect to mount.

EP 2532302 A1 discloses systems and methods for measuring an analyte in a host, and systems and methods for transcutaneous measurement of glucose in a host. The system includes applicator, a mounting unit, and an electronics unit. A force-locking mechanism is disclosed, configured to ensure a proper mate between the electronics unit and the mounting unit. A seal is formed between the mounting unit and the electronics unit, wherein an appropriate force is required to ensure a seal has sufficiently formed therebetween. In some circumstances, it can be advantageous to ensure the electronics unit has been properly mated, e.g. by snap-fit or sealingly mated, to the mounting unit. Accordingly, upon release of the applicator from the mounting unit after sensor insertion, and after insertion of the electronics unit into the mounting unit, the force-locking mechanism allows the user to ensure a proper mate and/or seal therebetween. In practice, a user pivots, e.g., lifts or twists, the force-locking mechanism such that it provides force on the electronics unit by pulling upon the circular tab. The force-locking mechanism is preferably released thereafter.

Thus, various types of sealed connection systems between the disposable sensor patch and the electronics unit of continuous monitoring systems are known in the art. These connection systems, however, in many cases imply some significant technical challenges or even shortcomings. Thus, generally, in most cases, cleaning is an issue. As an example, pin contacts with a radial seal or latches with an axial seal are generally difficult to clean due to a dead space inside the contacts. Further, user-friendly handling and, still, a high reliability of the electrical and mechanical connections provide technical challenges which have to be resolved by keeping the overall volume as low as possible, in order to increase the wearing comfort. As an example, latched axial seals, in many cases, require applying high closing forces.

Problem to be Solved

It is therefore an objective of the present invention to provide a sensor assembly and a method for detecting at least one analyte in a body fluid as well as a sensor patch assembly and an electronics unit for use in the sensor assembly which at least partially address the above-mentioned challenges and shortcomings of devices and methods of this kind. Specifically, a connection between a sensor patch and an electronics unit shall be provided which is mechanically and electrically reliable, which requires low handling forces and which and enables a simple cleaning process.

SUMMARY OF THE INVENTION

This problem is solved by the devices and the method with the features of the independent claims. Preferred embodiments, which might be realized in an isolated fashion or in any arbitrary combination are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, a sensor assembly for detecting at least one analyte in a body fluid is disclosed. The sensor assembly comprises at least one sensor patch, having at least one body mount configured for attachment to a body of a user; and at least one sensor for detecting the at least one analyte in the body fluid, the sensor having at least two electrodes configured for detecting the analyte, the sensor further having at least two sensor contacts for electrically contacting the electrodes, The sensor patch comprises a patch housing with a patch bayonet contour, preferably a patch bayonet screw.

The sensor assembly further comprises at least one electronics unit attachable to the body mount, having at least one electronics component for one or more of controlling the detection of the analyte or transmitting measurement data to another component. The electronics unit further comprises an electronics unit housing having an electronics unit bayonet contour, preferably an electronics unit bayonet screw.

The patch bayonet contour and the electronics unit bayonet contour in conjunction form a bayonet connector configured for establishing a releasable mechanical connection between the electronics unit and the sensor patch. As will be outlined in further detail below, the sensor patch and the electronics unit may further be designed such that, when the releasable mechanical connection between the electronics unit and the sensor patch is established, an electrical connection between the electronics unit and the sensor patch, specifically the sensor, is established.

As used herein, an "assembly" generally refers to a group of at least two elements which may interact in order to fulfill at least one common function. The at least two components may be handled independently or may be coupled, connectable or integratable in order to form a common component. Thus, a "sensor assembly" generally refers to a group of at least two elements or components which are capable of interacting in order to perform at least one sensor function, in the present case in order to perform at least one detection of the at least one analyte in the body fluid and/or in order to contribute to the at least one detection of the at least one analyte in the body fluid. The sensor assembly generally may also be referred to as a sensor system, a sensor kit or a sensor device.

The sensor assembly generally may be used for detecting at least one analyte in a body fluid of a user. Specifically, the sensor assembly may be used for long-term monitoring or continuous monitoring of an analyte concentration in the body fluid of the user, such as in a body fluid contained in a body tissue of the user. As generally used within the present invention, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the invention may be applied to other types of users or patients or diseases.

As further used herein, the term "body fluid" generally may refer to a fluid which typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids. During detection of the at least one analyte, the body fluid may be present within the body or body tissue. Thus, specifically, as will be outlined in further detail below, the sensor may be configured for detecting at least one analyte in a body tissue.

As further used herein, the term "analyte" may refer to an arbitrary element, component or compound which may be present in the body fluid and the presence and/or the concentration of which may be of interest for the user, the patient or medical staff such as a medical doctor. Particularly, the analyte may be or may comprise an arbitrary chemical substance or chemical compound which may take part in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte specifically may be an analyte-specific detection.

As further used herein, the term "detect" generally refers to the process of determining the presence and/or the quantity and/or the concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analogue signal and/or may be or may comprise at least one digital signal.

As further used herein, the term "determining a concentration" generally may refer to a process of generating at least one representative result or a plurality of representative results indicating the concentration of the analyte in the body fluid. As further used herein, the term "sensor" may generally refer to an arbitrary element which is adapted to perform the above-mentioned process of the detection and/or which is adapted to be used in the above-mentioned process of the detection. Thus, the sensor specifically may be adapted to determine the concentration of the analyte and/or a presence of the analyte.

The sensor may particularly be a transcutaneous sensor. As used herein, the term "transcutaneous sensor" generally refers to a sensor which is adapted to be fully or at least partly arranged within a body tissue of the patient or the user. For this purpose, the sensor generally may be dimensioned such that a transcutaneous insertion is feasible, such as by providing a width in a direction perpendicular to an insertion direction of no more than 5 mm, preferably of no more than 2 mm, more preferably of no more than 1.5 mm. The sensor may have a length of less than 50 mm, such as a length of 30 mm or less, e.g. a length of 5 mm to 30 mm. The term "length" as further used herein may be viewed in a direction parallel to the insertion direction. It shall be noted, however, that other dimensions are feasible. In order to further render the sensor to be usable as a transcutaneous sensor, the sensor may fully or partially provide a biocompatible surface, i.e. a surface which, at least during durations of use, do not have any detrimental effects on the user, the patient or the body tissue. As an example, the transcutaneous sensor may fully or partially be covered with at least one biocompatible membrane, such as at least one polymer membrane or gel membrane which is permeable for the at least one analyte and/or the at least one body fluid and which, on the other hand, retains sensor substances such as one or more test chemicals within the sensor and prevents a migration of these substances into the body tissue.

The sensor preferably may be an electrochemical sensor. As used herein, an "electrochemical sensor" generally is a sensor which is configured to conduct an electrochemical measurement in order to detect the at least one analyte contained in the body fluid. The term "electrochemical measurement" refers to a detection of an electrochemically detectable property of the analyte, such as an electrochemical detection reaction. Thus, for example, the electrochemical detection reaction may be detected by comparing one or more electrode potentials, as further discussed below. The electrochemical sensor specifically may be adapted to and/or may be usable to generate at least one electrical sensor signal which directly or indirectly indicates the presence and/or the extent of the electrochemical detection reaction, such as at least one current and/or at least one voltage. For this purpose, as will be outlined in further detail below, the at least one electrochemical sensor provides two or more electrodes, which also are referred to as a sensor electrodes. The detection may be analyte-specific. The measurement may be a qualitative and/or a quantitative measurement. Still, other embodiments are feasible.

As further used herein, the term "electrode" may generally refer to an arbitrary element which is configured to or which is usable to electrically or electrochemically detect the analyte. Specifically, each electrode may comprise at least one conductive pad or conductive element, such as at least one metal pad and/or at least one metal element and/or at least one pad or element made of at least one conductive inorganic or organic material such as carbon and/or a conductive polymer. The at least one conductive pad or conductive element may be uncovered and/or may be covered with at least one additional material, such as at least one sensor chemical, as will be outlined in further detail below. The at least two electrodes of the sensor may be embodied such that an electrochemical reaction may take place at one or more of the electrodes, such as one or more working electrodes. Thus, the electrodes may be embodied such that an oxidation reaction and/or reduction reaction may take place at one or more of the electrodes. The electrochemical detection reaction may be detected by comparing one or more electrode potentials, such as an electrostatic potential of a working electrode with an electrostatic potential of one or more further electrodes such as a counter electrode or a reference electrode. Generally, the two or more electrodes may be used for one or more of an amperometric, an amperostatic, a potentiometric or a potentiostatic measurement. These types of measurements generally are known to the skilled person in the art of analyte detection, such as from WO 2007/071562 A1 and/or the prior art documents disclosed therein. For potential setups of the electrodes, electrode materials or measurement setups, reference may be made to this document. It shall be noted, however, that other setups, electrode materials or measurement setups may be used within the present invention.

The at least two electrodes may comprise at least one working electrode. As used herein, the term "working electrode" refers to an electrode being adapted for or being usable for performing at least one electrochemical detection reaction for detecting the at least one analyte in the body fluid. The working electrode may have at least one test chemical being sensitive to the analyte to be detected. The working electrode may further comprise at least one conductive working electrode pad. The conductive working electrode pad may be in contact with the at least one test chemical. Thus, the at least one test chemical may be coated onto the at least one conductive working electrode pad. The at least one test chemical may form at least one test chemical surface which may be in contact with the at least one body fluid. As an example, the at least one test chemical surface may be an open test chemical surface or may be covered by the above-mentioned at least one membrane which is permeable to the at least one analyte to be detected and/or to the body fluid or a part thereof, such that the analyte may interact with the test chemical. For potential test chemicals and/or materials for the conductive working electrode pad, again, reference may be made to WO 2007/071562 A1 and/or the prior art documents disclosed therein. Other embodiments, however, are feasible.

The one or more "working electrode pads" specifically may be formed by at least one dot, line or grid which each can form a coherent area of an electrode material. If more than one dot, line or grid of the electrode material is superimposed, the sensor may provide more than one electrode pad. All electrode pads together may build the working electrode. The sensor may comprise the working electrode with a number of electrode pads in a range from 1 to 50, preferably from 2 to 30, preferably from 5 to 20 electrode pads.

The term "test chemical" specifically may refer to an arbitrary material or a composition of materials adapted to change at least one detectable property in the presence of at least one analyte. This property may be an electrochemically detectable property. Specifically, the at least one test chemical may be a highly selective test chemical, which only changes the property if the analyte is present in the body fluid whereas no change occurs if the analyte is not present. The degree or change of the at least one property is dependent on the concentration of the analyte in the body fluid, in order to allow a quantitative detection of the analyte. As an example, the test chemical may comprise at least one enzyme, such as glucose oxidase and/or glucose dehydrogenase.

The at least two electrodes may further comprise at least one counter electrode. As used herein, the term "counter electrode" refers to an electrode adapted for performing at least one electrochemical counter reaction and adapted for balancing a current flow required by the detection reaction at the working electrode. Additionally or alternatively the at least two electrodes may further comprise at least one reference electrode. The reference electrode may have a stable and well-known electrode potential. The electrode potential may preferably be highly stable. The counter electrode and the reference electrode may be one of a common electrode or two separate electrodes. Again, for potential materials usable for the counter electrode and/or the reference electrode, reference may be made to WO 2007/071562 A1 and/or the prior art documents disclosed therein. Other embodiments, however, are feasible.

The electrodes, particularly the working electrode, the counter electrode and/or the reference electrode, may have an identical dimension. The term "dimension" refers to one or more of a width, a length, a surface area, a shape of the first and the second electrodes. A shape of the electrodes may be determined by a manufacturing process, such as a cutting and/or a printing process. The shape may be rectangular or round. Still, other embodiments are feasible, such as embodiments in which the dimensions of the working electrode and the counter/reference electrodes differ and/or embodiments in which a non-circular shape or a non-rectangular shape is used. The electrodes may be made of a non-corrosive and non-passivating material. With regard to possible electrode materials, reference may be made to the prior art documents cited above.

The sensor may further comprise at least one substrate. The at least two electrodes and/or the at least two sensor contacts generally may be attached to the substrate. The sensor may further comprise at least two electrical traces which interconnect the electrodes and the sensor contacts and which may also be attached to the substrate. As used herein, the term "substrate" may generally refer to an arbitrary element which is suitable to carry one or more other elements disposed thereon or therein. As an example, the substrate may be a flat substrate, such as a substrate having a lateral extension exceeding its thickness by at least a factor of 2, at least a factor of 5, at least a factor of 10, or even at least a factor of 20 or more. The substrate specifically may have an elongated shape, such as a strip-shape and/or a bar-shape. The substrate, as an example, may comprise a shaft, specifically a shaft having an elongate shape. For example the shaft may have a shape selected from the group consisting of a strip, a needle, a tape. The substrate may comprise at least one contact portion. The substrate, as outlined above, may be an elongate substrate, with the electrodes being placed at one end of the elongate substrate and the sensor contacts, also referred to as "contact pads", being placed on an opposing end of the substrate. The contact pads may be located in the contact portion.

The substrate may be a flexible substrate, i.e. a substrate which may be bent or deformed by forces which usually occur during wearing and insertion into the body tissue, such as forces of 10 N or less. Specifically the substrate may be made of or may contain at least one deformable material, such as at least one plastic or malleable material and/or at least one elastic material. As an example, the substrate may be or may comprise at least one foil, such as at least one foil made of one or more of a paper material, a cardboard material, a plastic material, a metal material, a ceramic material or a glass material. As an example, the substrate may comprise at least one polyimide foil. The substrate specifically may comprise at least one electrically insulating material, such as at least one electrically insulating plastic foil.

As used herein, the term "sensor contact", also referred to as a "contact pad", generally refers to an element having an open or electrically contactable surface which is electrically conductive. As an example, the sensor contacts may be or may comprise at least one layer of at least one electrically conductive material which directly or indirectly may be deposited onto the substrate and which provides an electrically contactable surface. In a dimension or direction parallel to a surface of the substrate, the sensor contacts may provide a contact surface area, such as an area having a rectangular shape, a polygonal shape or a round shape. Other shapes are possible.

The sensor contacts may be located in the above-mentioned contact portion of the sensor. The sensor contacts may be fully or at least partially made of at least one metallic material. Thus, as an example, sensor contacts may comprise at least one gold layer. In addition or alternatively, other types of metal layers may be applied, such as at least one of: Cu, Ni, Ag, Au, Pd, Pt. Again, additionally or alternatively, the sensor contacts may fully or partially be made of at least one non-metallic electrically conductive material, such as at least one of: a conductive carbon material, such as graphite, graphene, carbon nanotubes, glassy carbon; an electrically conductive organic material, such as an electrically conductive polymer.

As further used herein, the term "electrical trace" may generally refer to an arbitrary electrically conducting element which is suited or configured to electrically connect at least two electrical elements, such as, in this case, at least one sensor contact with at least one associated electrode. Thus, for each electrode, at least one sensor contact may be associated and the electrode and the associated sensor contacts may be connected via the at least one electrical trace, thereby allowing for electrically contacting, independently, each electrode via the at least one associated sensor contact. The electrical traces specifically may have a shape at least in two dimensions. The electrical trace preferably may have an elongated shape, such as a length along the substrate exceeding a width in a plane of the substrate by at least a factor of 5, such as at least a factor of 10, or even at least a factor of 100. For example, the electrical trace may comprise at least one wire or path. Furthermore, the electrical trace may comprise at least one electrically conductive material. Preferably, the electrically conductive material may comprise copper. Additionally or alternatively, one or more of the materials listed above for the contact pads may be used. Further, the electrically conductive material may be or may comprise at least one material selected from the group consisting of: an electrically conductive organic material, preferably at least one electrically conductive polymer, an electrically conductive carbon material, preferably one or more of graphite, graphene, glassy carbon and carbon nanotubes; a metal preferably from the group consisting of Cu, Ni, Ag, Au, Pd and Pt. However, additionally or alternatively, one or more other electrically conductive materials may be used.

The sensor may further comprise at least one electrically insulating material. As further used herein, the term "electrically insulating material" may generally refer to a material having an electric conductivity below 0.001 S/cm, preferably below 0.0001 S/cm, most preferably below $10^{-6}$ S/cm, even more preferably below $10^{-8}$ S/cm, below $10^{-9}$ S/cm, below $10^{-10}$ S/cm or even below $10^{-11}$ S/cm. For example the electrically insulating material may comprise an insulating resist. However, other materials are feasible. The electrically insulating material may at least partially cover the electrical traces, the insulating material leaving open the electrodes and the contact pads. The electrically insulating material may comprise at least one insulating cover layer covering the electrical traces. The electrically insulating material may form openings, wherein the electrodes are located within the openings.

As further used herein, the term "body mount" generally refers to a device which is attachable to the skin of the user or patient. Thus, the body mount may comprise at least one attachment component which is capable of connecting the body mount to the skin, such as at least one adhesive surface and/or at least one adhesive strip or plaster. The body mount may further comprise at least one body mount housing, also referred to as a base, which may be used as a sensor support, for attachment of the sensor, such as the contact portion of the sensor. Thus, generally, the body mount may also be referred to as a sensor support.

As further used herein, the term "sensor patch" generally refers to the combination of the body mount and the sensor. Thus, these two components, in a connected state or in a disconnected state, as an assembly, may be referred to as the sensor patch.

As further used herein, the term "electronics unit" generally refers to an arbitrary device having at least one electronic component. The electronics unit specifically may be designed or used as a re-usable element, whereas the sensor patch often is designed as a disposable element. Specifically, the electronics unit may comprise at least one electronic component for one or more of performing a measurement with the sensor, performing a voltage measurement, performing a current measurement, recording sensor signals, storing measurement signals or measurement data, transmitting sensor signals or measurement data to another device. Other embodiments of the electronic components are feasible. The electronics unit specifically may comprise at least one circuit board having disposed thereon at least one electronics component, such as at least one active and/or at least one passive component. The electronics unit may further comprise at least one housing which fully or partially surrounds the electronics component. The electronics unit may further comprise at least one of an integrated circuit, a microcontroller, a computer or an application-specific integrated circuit (ASIC). The electronics unit may specifically be embodied as a transmitter or may comprise a transmitter, for transmitting data. Preferably, the electronics unit may be reversibly connectable to the body mount. Further, the combination of the electronics unit and the body mount may be referred to as a "control part" of the sensor assembly, in a connected or in a disconnected state.

As outlined above, the sensor patch comprises at least one patch housing, and the electronics unit comprises at least one electronics unit housing. As generally used herein, the term "housing" may generally refer to an arbitrary element which is adapted to fully or partially surround and/or receive one or more elements in order to provide one or more of a mechanical protection, a mechanical stability, an environmental protection against moisture and/or ambient atmosphere, a shielding against electromagnetic influences or the like. Thus, the housing may simply provide a basis for attachment and/or holding one or more further components or elements. Additionally or alternatively, the housing may provide one or more interior spaces for receiving one or more further components or elements. Consequently, the term "patch housing" may generally refer to a housing of the sensor patch. Thus, the patch housing may provide a basis for attachment and/or integration of one or more further components, such as the sensor or a part thereof. Similarly, the term "electronics unit housing" may generally refer to a housing of the electronics unit. Thus, the electronics unit housing may fully or partially surround one or more electronics components of the electronics unit and/or may hold one or more electronics components of the electronics unit. As an example, the electronics unit housing may fully or partially surround the at least one interior space located inside the electronics unit housing configured for receiving one or more of the electronics components of the electronic unit. The electronics unit housing, as an example, may contain one or more electronics unit housing base plates and one or more electronics unit housing covers which interact with the electronics unit housing base plate in order to form the interior space configured for receiving the one or more electronics components of the electronic unit. Other embodiments, however, are feasible.

Specifically, the housing may be configured to shield one or more elements of the sensor assembly from external influences like moisture and/or mechanical stress. The housing may be a watertight housing having an essentially round shape. Further, the housing may have an essentially flat surface. Specifically, the electronics unit may comprise an essentially flat base and the housing. The housing may cover the essentially flat base on a side opposing the body mount. The base may protrude from the housing, forming a rim which fully or partially surrounds the electronics unit. The rim may be configured to be engaged by the body mount. The housing, in general, may comprise one or more parts.

As outlined above, the patch housing comprises at least one patch bayonet contour, and the electronics unit comprises at least one electronics unit bayonet contour. The patch bayonet contour and the electronics unit bayonet contour, in conjunction, form a bayonet connector configured for establishing a releasable mechanical connection between the electronics unit and the sensor patch. As generally used herein, the term "bayonet contour" generally refers to a component or part of an element which is configured to interact with a counterpart bayonet contour in order to form a bayonet connection or a bayonet connector. Thus, the patch bayonet contour and the electronics unit bayonet contour may be complementary bayonet contours configured for forming a bayonet connection or, in conjunction, a bayonet connector. Therein, one of the patch bayonet contour or the electronics unit bayonet contour may be or may comprise a male bayonet contour, such as a male bayonet plug, and the other one of the patch bayonet contour of the electronics unit bayonet contour may be or may comprise a female bayonet contour, such as a female bayonet plug. As generally used herein, a bayonet connector, also referred to as a bayonet connection, may generally refer to an arbitrary connector or connection between two bayonet contours in a bayonet fashion.

Therein, generally, one or both of the bayonet contours involved may comprise at least one protrusion and, in a complementary fashion, the other one of the bayonet contours may comprise at least one bayonet grove or bayonet slot in which the protrusion may be guided two bayonet contours interact in order to form the bayonet connection or bayonet connector. The bayonet grove or bayonet slot generally may comprise at least two different sections. In a first section, the protrusion may simply be moved in an essentially axial fashion, such as at an angle of no more than 20°, e.g. no more than 10°, no more than 5° or even 0° with respect to an axis which interconnects the two bayonet contours. Thus, as an example, while the protrusion is guided in the first section, the two components which will be interconnected by the bayonet connector or bayonet connection simply may be pushed together along the axis. In a second section, which directly or indirectly may follow the first section, the protrusion may be guided in a spiral or screw-like fashion around the axis. The bayonet grove or bayonet slot may comprise one or more further sections, such as one or more sections before the first section, one or more intermediate sections in between the first section and the second section or one or more sections behind the second section. Combinations of the named sections are feasible. Thus, as an example, the interconnection of the electronics unit and the sensor patch may be performed by a sequence of movements or relative movements of these two components, such as a first linear movement along the axis and, subsequently, a rotational movement.

When releasing the bayonet connector or bayonet connection, the movements may be performed in the opposite order. Thus, as an example, the rotational movement may be performed and, subsequently, a linear movement may be performed, by pulling the electronics unit and the sensor patch apart along the axis.

It shall be noted that one of the patch bayonet contour or the electronics unit bayonet contour may comprise the at least one protrusion, and the other one of the patch bayonet contour or the electronics unit may comprise the complementary bayonet grove or bayonet slot. However, mixtures are feasible. As an example, the patch bayonet contour may comprise at least one protrusion and at least one bayonet grove or bayonet slot, and, in a complementary fashion, the electronics unit bayonet contour may comprise at least one bayonet grove or bayonet slot and at least one protrusion.

Thus, generally, the establishing of the releasable mechanical connection by using the bayonet connector may imply a combination of an axial movement and a rotational movement, in a subsequent fashion, with preferably the axial movement preceding the rotational movement. The rotational movement, as an example, may imply pivoting the electronics unit with respect to the sensor patch or vice a versa, about the axis. The axis, as an example, may be a rotational axis of the bayonet connector, such as an axis of symmetry of the bayonet connector. The axis, as an example, may be perpendicular to a base plate of the sensor patch, such as perpendicular to a skin surface of the user. The tilting, as an example, may take place about a tilting angle, from an initial angle to a final angle, wherein, in the final angle, as an example, the electronics unit is locked to the sensor patch. The tilting angle, for example, may be an angle in the range of 40° to 240°, such as an angle of 50° to 130°, e.g. an angle of 90°.

As used herein, the term "mechanical connection" generally refers to a connection of two or more components by mechanical holding forces. As an example, the mechanical connection may be or may comprise at least one of a form-fit or a force-fit connection. In the case of the bayonet connector or bayonet connection, specifically, the mechanical connection may be a form-fit connection. As further used herein, the term "releasable", in the context of the mechanical connection, generally refers to the fact that the mechanical connection may be brought from a disconnected state, also referred to as a non-mated state, into a connected state, also referred to as a mated state, and back into the disconnected state. Thus, the mechanical connection may be closed and released at will. Specifically, the mechanical connection may be releasable without using any tools, simply by manual action. As an example, for opening the bayonet connector, forces of no more than 50 N, such as of no more than 20 N, such as of no more than 10 N, may be required, which may be applied by one hand or even the fingers or fingertips of the user.

The use of the bayonet connector for interconnecting the sensor patch and the electronics unit implies a large number of advantages. Generally, bayonet connectors are easily accessible and, thus, are quite simple to clean and to keep clean, e.g. by using wipers, brushes, disinfecting sprays or cotton swabs. Further, bayonet connectors may be built rather small and, thus, do not unnecessarily increase the volume of the control part. Further, as will be outlined in further detail below, the bayonet connector may fully or partially surround an electrical connection between the electronics unit and the sensor patch and, thus, may provide protection of this electrical connection against external influences such as mechanical influences and/or humidity. Further, as compared to other mechanical connection elements, the bayonet connector generally may be closed or released by using a relatively low amount of force applied by the user. The latter is specifically advantageous in the case of diabetes monitoring, since, in many cases, elderly users, handicapped users or children may not be capable of bringing up the required manual force or fine motoric skills for handling more complex interconnecting devices. Still, bayonet connectors are generally known to be reliable and mechanically robust, since these bayonet connectors are used in a wide variety of small-sized, mid-sized or large mechanical interconnections such as in cameras. Further, in bayonet connectors, manufacturing or handling tolerances may be compensated for, since the bayonet contours, specifically the above-mentioned bayonet grove or bayonet slot, may be designed to tolerate misalignments and/or manufacturing tolerances by guiding the complementary bayonet contour in an appropriate way, such as from a high tolerance region into a tight tolerance region, and, thereby, may still provide a robust and precise mechanical interconnection. These highly tolerance capabilities further allow for miniaturization of the mechanical interconnection between the electronics unit and the sensor patch.

As outlined above, when establishing the mechanical connection by using the bayonet connector, additionally, such as simultaneously with establishing the mechanical connection, an electrical connection between the electronics unit and the sensor patch, such as the sensor, may be established. Thus, the electronics unit further may comprise at least two electrical contacts adapted for directly or indirectly contacting the sensor, such as the contact pads or sensor contacts of the sensor. In a mated state, in which the releasable mechanical connection between the electronics unit and the sensor patch is established by the bayonet connector, an electrical connection between the sensor contacts and the electrical contacts of the electronics unit may be established. The establishing of the electrical connection and the establishing of the mechanical connection may take place simultaneously. Other embodiments, however, are feasible.

As used in the context of the electrical contacts of the electronics unit, the term "electrical contacts" simply refers to electrically conductive elements which may be electrically contacted by at least one other electrical component. As an example, the electrical contacts of the electronics unit may be or may comprise two or more contact pads, two or more spring contacts, two or more electrical contact pins or combinations thereof. The electrical contacts of the electronics unit may be located on a lower side of the electronics unit which, in a mated state, faces the sensor patch. As an example, the electronics unit may have an essentially flat lower side which may rest on an upper side of front side of the sensor patch.

The electrical connection between the sensor contacts and the electrical contacts of the electronics unit simply may imply a connection in which these two electrical components are pressed onto each other. Thus, as an example, the electrical contacts of the electronics unit may be pressed onto the sensor contacts and/or vice a versa. The force required for pressing these electrical components onto one another may be built up during establishing the bayonet connection, and the holding force for holding the electrical components in a compressed state may be absorbed by the bayonet connector.

As outlined above, a further advantage of the bayonet connector may be the fact that the bayonet connector may protect one or more regions or components which are located inside the bayonet connector. Thus, as an example, the electrical connection established between the electrical contacts of the electronics unit and the sensor contact of the sensor may fully or partially be located inside the bayonet connector and may fully or partially be surrounded by the bayonet connector. As an example, in the mated state, the bayonet connector at least partially may surround the electrical connection between the sensor contacts and the electrical contacts of the electronics unit. Thus, the bayonet connector may protect the electrical connection from mechanical influences and/or from detrimental environmental influences such as humidity and/or sweat.

Further optional details of the sensor assembly may refer to the electrical connection between the sensor contacts and the electrical contacts of the electronics unit. As outlined above, various ways of contacting are feasible. The electrical contact may be established in a direct way, by directly contacting the sensor contacts with the electrical contacts of the electronics unit and/or by interposing at least one conductive element in between the sensor contacts and the electrical contacts of the electronics unit. As an example, the electrical connection between the sensor contacts and the electrical contacts of the electronics unit may be established by at least one of: an electrically conductive rubber material; an anisotropic electrically conductive rubber material; a Zebra connector; an electrically conductive spring contact; a flexible printed circuit (FPC) connector; a contact pin. These electrically conductive elements which may be one or both of fully or partially integrated into one or both of the sensor contacts or the electrical contacts of the electronics unit or fully or partially be embodied as at least one separate conductive element, are generally known to the skilled person, such as in the field of electrically connecting printed circuit boards, displays or the like. The term "Zebra connector" generally refers to an anisotropic conductive material which provides, in a matrix material which generally is an insulating material, one, two or more electrically conductive traces, such as for providing electrically connecting paths from an upper side of the Zebra connector to a lower side or vice versa, e.g. in a stripe-shaped fashion having interdigitated conductive and non-conductive stripes. These elements are commercially available e.g. for contacting displays or circuit boards.

A flexible printed circuit connector, also referred to as an FPC connector, is a connector which is typically used for interconnecting one or more flexible circuit boards or flexible cables. As an example, these types of connectors may be used for mounting electronic devices on flexible substrate, such as flexible plastic substrates, or vice versa. Specifically, the sensor patch may comprise at least one FPC connector, wherein the sensor, specifically a contact portion of the sensor, may be connected to the FPC connector, such as plucked into the FPC connector. The FPC connector may then electrically contact the electronics unit once the mechanical connection by using the bayonet connector is established. The FPC connector may fully or partially be surrounded by the bayonet connector. Thus, generally, the sensor may be plugged into a flexible printed circuit connector, and the electrical connection may directly or indirectly be established between the flexible printed circuit connector and the electronics unit. The electrical connection may indirectly be established between the flexible printed circuit connector and the electronics unit via at least one circuit board, preferably via at least one circuit board having one or more spring contacts contacting the electronics unit. Other contacting means, however, are feasible.

As outlined above, the bayonet connector specifically may be used for pressing the electronics unit onto the sensor patch or vice a versa and/or for keeping the electronics unit pressed onto the sensor patch or vice a versa, once the releasable mechanical connection is established. Thus, in a mated state, in which the releasable mechanical connection between the electronics unit and the sensor patch is established by the bayonet connector, the electronics unit may be pressed onto the sensor patch or vice versa, by means of the bayonet connector.

As outlined above, the bayonet connector may further fulfill the function of protecting one or more regions and/or components of the control part once the releasable mechanical connection is established. These one or more regions and/or components which may be protected by the bayonet connector may fully or partially be surrounded by the bayonet connector. Additionally or alternatively, however, the control part may further comprise one or more sealing elements which may protect one or more components of the control part from external influences, such as from humidity and/or sweat. As an example, the above-mentioned electrical connection may be protected by one or more sealing elements which may be interposed in between the sensor patch and the electronics unit. Thus, generally, the sensor assembly may further comprise at least one sealing element configured for sealing off at least one region in between the sensor patch and the electronics unit when the releasable mechanical connection between the electronics unit and the sensor patch is established. The at least one sealing element may be part of at least one element selected from the group consisting of: the patch housing; the electronics unit housing; the patch bayonet contour; the electronics unit bayonet contour; a connector element carrying the sensor. Combinations of these options are feasible.

As used herein, the term "sealing element" may generally refer to an arbitrary element which is configured to seal off one or more elements from external influences, such as from one or more of humidity or moisture, ambient air or other detrimental media, specifically fluid media. The sealing element specifically may comprise one or more sealing rings. As used herein, the term "sealing ring" generally may refer to an arbitrary sealing element which is configured to surround one or more elements to be sealed off from environmental influences such as moisture. Specifically, the sealing ring may be configured to surround the at least one element to be sealed off from the environmental influences in at least two dimensions. Thus, the sealing ring may be a ring-shaped element. The ring-shaped element may have the shape of a circular ring, a polygonal ring, an oval ring or any other closed shape. The sealing ring specifically may be made of at least one compressible material.

The sealing element preferably may be or may comprise a compressible sealing element, such as a flexible or inelastic sealing element. Thus, the sealing element may be or may comprise at least one compressible material, such as at least one flexible and/or inelastic material. As an example, the sealing element may fully or partially be made of a plastic material which is flexible and/or deformable, such as at least one elastomeric material. As an example, one or more of a rubber material, a silicone material or a foamed plastic material may be used.

As outlined above, the sealing element may fully or partially be designed as a separate sealing element which may simply be handled independently from the sensor patch and the electronics unit, such as by interposing this sealing element in between the sensor patch and the electronics unit when mounting the electronics unit to the sensor patch. Still, additionally or alternatively, the sealing element may fully or partially be designed as an integral component of one or both of the sensor patch or the electronics unit. In the latter case, the at least one sealing element may at least partially be integrated into the at least one element by multicomponent molding, preferably by multicomponent injection molding and/or by insert molding. Other ways of integrating are feasible, however.

The sealing element, as outlined above, specifically may be or may comprise at least one ring-shaped sealing element, i.e. a sealing ring. Thus, as an example, the sealing ring simply may comprise at least one O-ring. As outlined above, the at least one sealing element, specifically the at least one sealing ring, may seal off one or more regions in between the sensor patch and the electronics unit. Specifically, as also discussed above, the region in between the sensor patch and the electronics unit which is sealed off by the sealing element may comprise the at least one optional electrical connection between the sensor contacts and the electronics unit. The at least one sealing element may fully or partially, i.e. at least partially, surround the electrical connection between the sensor contacts and the electronics unit.

The use of the at least one sealing element, such as the at least one sealing ring, in conjunction with the bayonet connector, may be designed in a rather advantageous fashion, since the bayonet connector may be used for positioning and/or centering the sealing element when the mechanical connection is established. Thus, the bayonet connector may be configured to self-center the sealing element when the releasable mechanical connection is formed. As used herein, the term "self-centering" generally refers to an automatic positioning of an element, specifically an automatic centering with respect to an axis, such as the above-mentioned axis of the bayonet connector. During establishing the mechanical connection by using the bayonet connector, the sealing element may automatically be brought into the right position, such as by providing one or more guiding surfaces within the bayonet connector, such as within the patch bayonet contour and/or within the electronics unit bayonet contour. Generally, the bayonet connector may comprise at least one angled surface, such as at least one conical surface, wherein, when the releasable mechanical connection is formed, the sealing element is pressed onto the angled surface. The angled surface and the sealing element may form a sealing contour, e.g. with the sealing element interposed there between.

Thereby, generally, the electronics unit may be fairly easy to connect to the sensor patch, since the bayonet connector generally may allow for closing a seal with reduced force as compared to known connection means. By using the sealing element and the bayonet connector in conjunction, further, a very small system may be built up which is easy to handle even by handicapped, elderly or very young users. Further, as outlined above, by using self-aligning or self-centering contours, manufacturing tolerances may be compensated for.

The sensor may directly or indirectly be attached to the body mount. Specifically, the sensor may be attached to at least one connector element, and the connector element may be connectable or even connected to the body mount. As used herein, the term "connector element" may refer to an arbitrary element which is configured for connecting the sensor to the body mount. As an example, the connector element may comprise at least one base to which the sensor may be connected and/or into which the sensor may partially be inserted, such as with at least one connector portion of the sensor, and at least one connecting means for connecting the connector element to the base. The use of a separate connector element which is connectable to the body mount may provide the advantage that the body mount and the sensor may be handled independently and the sensor may be connected to the body mount during insertion of the sensor into the body tissue of the user.

The sensor patch, as outlined above, comprises at least one patch housing with the patch bayonet contour being part of the patch housing. The connector element, in a connected state, may also form part of the patch housing. Thus, the body mount may comprise a body mount housing, and the connector element may comprise a connector element housing, and the body mount housing in conjunction with the connector element housing may form the patch housing. As outlined above, the patch bayonet contour is part of the patch housing. Consequently, the patch bayonet contour may fully or partially be embodied within the body mount housing or, additionally or alternatively, may fully or partially be embodied within the connector element housing. Thus, as an example, the connector element may comprise the patch bayonet contour and/or a part thereof. Additionally or alternatively, however, the body mount may comprise the patch bayonet contour and/or a part thereof.

As outlined above, the optional connector element may be connectable to the body mount. Specifically, the connection may take place by one or more connecting means which. As an example, the connector element may be connectable to the body mount by one or both of a form-fit or a force-fit connection, preferably by at least one clip and/or by at least one snap fit connection. Thus, the connector element may comprise one or more hooks and/or one or more catches for forming a snap fit connection, and the body mount may comprise one or more corresponding cokes and/or catches for forming the snap fit connection, in conjunction with the connector element.

The body mount may comprise a base having a back side attachable to the body of the user and a front side facing the electronics unit. The connector element specifically may be connectable to the front side. The base may comprise at least one through hole, which may extend from the front side to the back side. The sensor may extend through the through hole and may protrude from the sensor patch assembly on the back side, in order to extend into a body tissue of the user.

The sensor assembly may further comprise at least one slide configured to hold the connector element with the sensor attached thereto and to connect the connector element to the body mount. As used herein, the term "slide", also referred to as a "slider", generally refers to an element which is guided in a slidable fashion, such as by one or more slide rails or slide guides. The slide may comprise a releasable connector for engaging the connector element with the sensor attached thereto, in order to hold the connector element before the connector element is connected to the body mount. The slide may be guided in a slidable fashion in such a way that the slide moves towards the body mount and transfers the connector element. Once the connecting means of the connector element engaged with corresponding connecting means of the body mount, the slide may release the connector element in order to move back from the body mount with the connector element and the sensor remaining attached to the body mount.

The slide specifically may be part of an insertion device, which may also be part of the sensor assembly. Thus, the sensor assembly generally may further comprise at least one insertion device for at least partially inserting the sensor into a body tissue of the user. The slide may be part of the insertion device. The insertion device may be configured for moving the slide towards the body mount during insertion.

For moving the slide, the insertion device may comprise one or more actuators. Specifically, the insertion device may comprise at least one lever for actuation by the user and for inserting the sensor into the body tissue.

The sensor assembly may be configured such that either the insertion device or the electronics unit may be mounted to the body mount. For mounting the insertion device to the body mount, the same or similar mounting techniques may be used as for mounting the electronics unit to the body mount. Thus, as an example, the insertion device may further comprise at least one insertion device housing having an insertion device bayonet contour. The insertion device bayonet contour may be configured for establishing a releasable mechanical connection between the insertion device and the sensor patch. Thus, the above-mentioned advantages of the bayonet connector may also be transferred to a connection between the insertion device and the body mount, since releasing a bayonet connector is fairly simple to manage even by handicapped, elderly or very young users.

The insertion device may further comprise at least one insertion cannula. The sensor may be receivable in the insertion cannula when the connector element is held by the slide. The insertion cannula specifically may be attached to the slide.

In a further aspect of the present invention, a sensor patch is disclosed which is designed and configured for use in a sensor assembly according to the present invention, such as according to one or more of the embodiments disclosed above or disclosed in further detail below. The sensor patch comprises:

at least one body mount configured for attachment to a body of a user; and at least one sensor for detecting the at least one analyte in the body fluid, the sensor having at least two electrodes configured for detecting the analyte, the sensor further having at least two sensor contacts for electrically contacting the electrodes, wherein the sensor patch comprises a patch housing with a patch bayonet contour, preferably a patch bayonet screw, for establishing a releasable mechanical connection between the electronics unit and the sensor patch.

For further details, specifically details about the patch bayonet contour, reference may be made to the disclosure of the sensor assembly above.

In a further aspect of the present invention, and electronics unit is disclosed, which is designed and configured for use in a sensor assembly according to the present invention, such as according to any one of the embodiments disclosed above or disclosed in further detail below. The electronics unit comprises at least one electronics component for one or more of controlling the detection of the analyte or transmitting measurement data to another component. The electronics unit further comprises an electronics unit housing having an electronics unit bayonet contour, preferably an electronics unit bayonet screw, for establishing a releasable mechanical connection between the electronics unit and the sensor patch.

For further details, specifically details regarding the electronics unit bayonet contour, reference may be made to the disclosure of the sensor assembly above.

In a further aspect of the present invention, a method for producing a sensor assembly for detecting at least one analyte in a body fluid is disclosed. The method specifically may be performed by using one or more of the sensor assembly, the sensor patch assembly or the electronics unit according to the present invention, such as disclosed in one or more of the embodiments given above and/or in one or more of the embodiments disclosed in further detail below. The method comprises the following method steps. The method steps may be performed in the given order. However, a different order is also feasible. Further, two or more or even all of the method steps may be performed in parallel or in a timely overlapping fashion. Further, one, more than one or even all of the method steps may be performed repeatedly. The method may comprise one or more additional method steps which are not disclosed.

The method comprises the following method steps:

Providing at least one sensor patch, having
- at least one body mount configured for attachment to a body of a user; and
- at least one sensor for detecting the at least one analyte in the body fluid, the sensor having at least two electrodes configured for detecting the analyte, the sensor further having at least two sensor contacts for electrically contacting the electrodes, wherein the sensor patch comprises a patch housing with a patch bayonet contour, preferably a patch bayonet screw;

providing at least one electronics unit attachable to the body mount, having at least one electronics component for one or more of controlling the detection of the analyte or transmitting measurement data to another component, wherein the electronics unit further comprises an electronics unit housing having an electronics unit bayonet contour, preferably an electronics unit bayonet screw;

establishing a releasable mechanical connection between the electronics unit and the sensor patch by using a bayonet connector formed by the patch bayonet contour and the electronics unit bayonet contour.

For details and definitions, reference may be made to the disclosure of the sensor assembly given above.

The proposed sensor assembly, the proposed sensor patch, the proposed electronics unit and the proposed method for producing a sensor assembly provide many advantages over known devices and methods.

A sealing for sealing off the at least one region between the sensor patch and the electronics unit may be realized via the angled surface. Therefore, contact areas may be realized without undercuts, which may easily be cleanable. In combination with the bayonet connector high tensile forces at low operating forces may be realizable. The angled surface may additionally offer the self-centering. Specifically, electrically conductive rubber materials may be applied. A number of required components may be reduced which may lead to cost reduction.

For mounting the sensor into the connector element the contact portion of the sensor may be put into a receptacle of the connector element. During this step, the sensor may be formed straightly and may not have its curved shape. As soon as the sensor may be placed in the receptacle gaps may be closed via adhesive materials. Specifically, photoactive adhesive materials may be applied. Therefore, the connector element housing may be made of a transparent material. Thereafter, the electrically conductive rubber material may be placed into a further receptacle of the connector element.

The electronics unit may connected to the body mount be via the electronics unit bayonet contour. Therefore, the electronics unit may be put on the body mount and rotated around a rotation angle.

A movement of the electronics unit in a direction of the body mount may be realized via the electronics unit bayonet contour. Through the angled surfaces of electronics unit bayonet contour high forces within this direction at a low rotational torque may be realizable. This may lead to an easy handling for the user. Further, high sealing forces and an automated self-centering of the sealing element may be realized. The sealing element may be mounted directly onto the connector element or may be produced by two component injection molding. Alternative cross-sections of the sealing element in comparison to a round cross-section may be applicable as well. The electronics unit may comprise smooth surfaces without undercuts and/or tight holes. The electrical contacts may have smooth surfaces and may easily be cleanable.

The body mount may comprise at least one finger rest. The electronics unit may have a corresponding receptacle for the finger rest such that the electronics unit may only be attachable in one orientation. Additionally, the finger rest may provide an attachment of the electronics unit with two fingers without a need to make use of a bond strength of the plaster. A blind application, specifically on a back of the user may, be facilitated.

Before usage, the connector element may be inserted into the insertion element housing, specifically a security container, with the insertion cannula. Within the insertion element housing may also be the slide which may specifically be stored in a movable manner. The connector element comprising the sensor and the electrically conductive rubber material may be hold in position by the slide via a detachable connection. Before usage, the slide may be located at an upper end of the insertion element housing. For moving the slide, the lever which may specifically be pivoted, may be applied. The connector element may specifically comprise hooks for attaching to the body mount. The hooks of the connector element may be connected to corresponding hooks of the body mount at a lowest position of the lever and a form-fit connection may be formed. During withdrawing of the slide, the slide may be removed from the connector element. The slide may be locked in place at an upper position within the insertion element housing when the cannula is completely withdrawn. Thereafter, the insertion element may be withdrawn from the sensor patch and may be disposed.

The sensor may be placed into the flexible printed circuit connector which may be placed on the circuit board and may comprise spring contacts on a side opposing the circuit board. The connector element may be connected to the electronics unit via the spring contacts. The sensor may be realized in a slim fashion at the contact portion. By applying the bayonet connector which may comprise the sealing element, only close tolerances may have to be compensated. By applying customary components of the connector element in combination with the bayonet connector the components may be produced via common processes. Therefore, the sensor assembly may specifically be a robust system.

Summarizing the findings of the present invention, the following embodiments are preferred:

Embodiment 1

A sensor assembly for detecting at least one analyte in a body fluid, comprising:
at least one sensor patch, having
at least one body mount configured for attachment to a body of a user; and at least one sensor for detecting the at least one analyte in the body fluid, the sensor having at least two electrodes configured for detecting the analyte, the sensor further having at least two sensor contacts for electrically contacting the electrodes,
wherein the sensor patch comprises a patch housing with a patch bayonet contour, preferably a patch bayonet screw;
at least one electronics unit attachable to the body mount, having at least one electronics component for one or more of controlling the detection of the analyte or transmitting measurement data to another component, wherein the electronics unit further comprises an electronics unit housing having an electronics unit bayonet contour, preferably an electronics unit bayonet screw;
wherein the patch bayonet contour and the electronics unit bayonet contour in conjunction form a bayonet connector configured for establishing a releasable mechanical connection between the electronics unit and the sensor patch.

Embodiment 2

The sensor assembly according to the preceding embodiment, wherein the electronics unit further comprises at least two electrical contacts, wherein, in a mated state, in which the releasable mechanical connection between the electronics unit and the sensor patch is established by the bayonet connector, an electrical connection between the sensor contacts and the electrical contacts of the electronics unit is established.

Embodiment 3

The sensor assembly according to the preceding embodiments, wherein in the mated state, the bayonet connector at least partially surrounds the electrical connection between the sensor contacts and the electrical contacts of the electronics unit.

Embodiment 4

The sensor assembly according to any one of the two preceding embodiments, wherein the electrical connection between the sensor contacts and the electrical contacts of the electronics unit is established by at least one of: an electrically conductive rubber material; an anisotropic electrically conductive rubber material; a Zebra connector; an electrically conductive spring contact; a flexible printed circuit (FPC) connector; a contact pin.

Embodiment 5

The sensor assembly according to any one of the three preceding embodiments, wherein the sensor is plugged into a flexible printed circuit connector, wherein the electrical connection is directly or indirectly established between the flexible printed circuit connector and the electronics unit.

Embodiment 6

The sensor assembly according to the preceding embodiment, wherein the electrical connection is indirectly established between the flexible printed circuit connector and the electronics unit via at least one circuit board, preferably via at least one circuit board having one or more spring contacts contacting the electronics unit.

Embodiment 7

The sensor assembly according to any one of the preceding embodiments, wherein in a mated state, in which the releasable mechanical connection between the electronics unit and the sensor patch is established by the bayonet connector, the electronics unit is pressed onto the sensor patch or vice versa, by means of the bayonet connector.

Embodiment 8

The sensor assembly according to any one of the preceding embodiments, wherein the sensor assembly further comprises at least one sealing element configured for sealing off at least one region in between the sensor patch and the electronics unit when the releasable mechanical connection between the electronics unit and the sensor patch is established.

Embodiment 9

The sensor assembly according to the preceding embodiment, wherein the at least one sealing element is part of at least one element selected from the group consisting of: the patch housing; the electronics unit housing; the patch bayonet contour; the electronics unit bayonet contour; a connector element carrying the sensor.

Embodiment 10

The sensor assembly according to the preceding embodiment, wherein the at least one sealing element is at least partially integrated into the at least one element by multi-component molding, preferably by multicomponent injection molding and/or by insert molding.

Embodiment 11

The sensor assembly according to any one of the three preceding embodiments, wherein the sealing element comprises at least one sealing ring.

Embodiment 12

The sensor assembly according to the preceding embodiment, wherein the sealing ring comprises at least one O-ring.

Embodiment 13

The sensor assembly according to any one of the five preceding embodiments, wherein the region in between the sensor patch and the electronics unit which is sealed off by the sealing element comprises at least one electrical connection between the sensor contacts and the electronics unit, wherein preferably the at least one sealing element at least partially surrounds the electrical connection between the sensor contacts and the electronics unit.

Embodiment 14

The sensor assembly according to any one of the six preceding embodiments, wherein the bayonet connector is configured to self-center the sealing element when the releasable mechanical connection is formed.

Embodiment 15

The sensor assembly according to the preceding embodiment, wherein the bayonet connector comprises at least one angled surface, preferably at least one conical surface, wherein, when the releasable mechanical connection is formed, the sealing element is pressed onto the angled surface.

Embodiment 16

The sensor assembly according to the preceding embodiment, wherein the angled surface and the sealing element form a sealing contour.

Embodiment 17

The sensor assembly according to any one of the preceding embodiments, wherein the sensor is attached to at least one connector element, wherein the connector element is connectable to the body mount.

Embodiment 18

The sensor assembly according to the preceding embodiment, wherein the connector element comprises the patch bayonet contour.

Embodiment 19

The sensor assembly according to any one of the two preceding embodiments, wherein the connector element is connectable to the body mount by one or both of a form-fit or a force-fit connection, preferably by at least one clip and/or by at least one snap fit connection.

Embodiment 20

The sensor assembly according to any one of the three preceding embodiments, wherein the body mount comprises a base having a back side attachable to the body of the user and a front side facing the electronics unit, wherein the connector element is connectable to the front side.

Embodiment 21

The sensor assembly according to the preceding embodiment, wherein the base comprises at least one through hole, wherein the sensor extends through the through hole and protrudes from the sensor patch assembly on the back side, in order to extend into a body tissue of the user.

Embodiment 22

The sensor assembly according to any one of the five preceding embodiments, the sensor assembly further comprising at least one slide, wherein the slide is configured to hold the connector element with the sensor attached thereto and to connect the connector element to the body mount.

Embodiment 23

The sensor assembly according to the preceding embodiment, wherein the sensor assembly further comprises at least one insertion device for at least partially inserting the sensor into a body tissue of the user, wherein the slide is part of the insertion device and wherein the insertion device is configured for moving the slide towards the body mount during insertion.

Embodiment 24

The sensor assembly according to the preceding embodiment, wherein the insertion device comprises at least one lever for actuation by the user and for inserting the sensor into the body tissue.

Embodiment 25

The sensor assembly according to any one of the two preceding embodiments, wherein the insertion device further comprises at least one insertion device housing having an insertion device bayonet contour, wherein the insertion device bayonet contour is configured for establishing a releasable mechanical connection between the insertion device and the sensor patch.

Embodiment 26

The sensor assembly according to any one of the three preceding embodiments, wherein the insertion device further comprises at least one insertion cannula, wherein the sensor is receivable in the insertion cannula when the connector element is held by the slide.

Embodiment 27

The sensor assembly according to the preceding embodiment, wherein the insertion cannula is attached to the slide.

Embodiment 28

A sensor patch for use in a sensor assembly according to any one of the preceding embodiments, having
- at least one body mount configured for attachment to a body of a user; and
- at least one sensor for detecting the at least one analyte in the body fluid, the sensor having at least two electrodes configured for detecting the analyte, the sensor further having at least two sensor contacts for electrically contacting the electrodes, wherein the sensor patch comprises a patch housing with a patch bayonet contour, preferably a patch bayonet screw, for establishing a releasable mechanical connection between the electronics unit and the sensor patch.

Embodiment 29

An electronics unit for use in a sensor assembly according to any one of the preceding embodiments referring to a sensor assembly, having at least one electronics component for one or more of controlling the detection of the analyte or transmitting measurement data to another component, wherein the electronics unit further comprises an electronics unit housing having an electronics unit bayonet contour, preferably an electronics unit bayonet screw, for establishing a releasable mechanical connection between the electronics unit and the sensor patch.

Embodiment 30

A method for producing a sensor assembly for detecting at least one analyte in a body fluid, the method comprising:
  providing at least one sensor patch, having
    at least one body mount configured for attachment to a body of a user; and
    at least one sensor for detecting the at least one analyte in the body fluid, the sensor having at least two electrodes configured for detecting the analyte, the sensor further having at least two sensor contacts for electrically contacting the electrodes,
  wherein the sensor patch comprises a patch housing with a patch bayonet contour, preferably a patch bayonet screw;
    providing at least one electronics unit attachable to the body mount, having at least one electronics component for one or more of controlling the detection of the analyte or transmitting measurement data to another component, wherein the electronics unit further comprises an electronics unit housing having an electronics unit bayonet contour, preferably an electronics unit bayonet screw;
    establishing a releasable mechanical connection between the electronics unit and the sensor patch by using a bayonet connector formed by the patch bayonet contour and the electronics unit bayonet contour.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

In the Figures:

FIG. 7 shows a further exemplary embodiment of a sensor patch of the second exemplary embodiment of the sensor assembly, in a perspective view;

FIGS. 8A and 8B show an exemplary embodiment of a connector element an assembled state (FIG. 8A) and in a disassembled state (FIG. 8B), of the second exemplary embodiment of the sensor assembly;

DETAILED DESCRIPTION OF THE EMBODIMENTS

Figure 1:
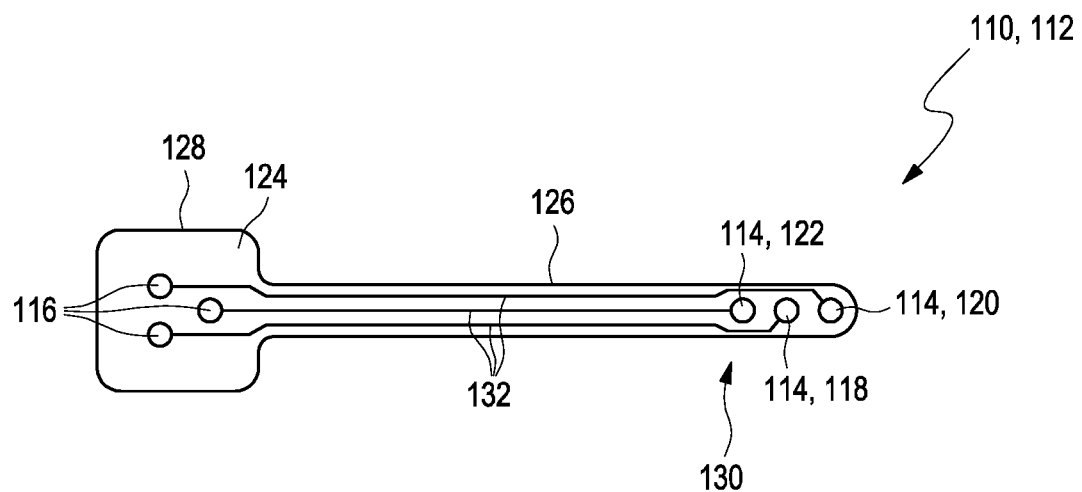
FIG. 1 shows an exemplary embodiment of a sensor in a top view.
Figure 2:
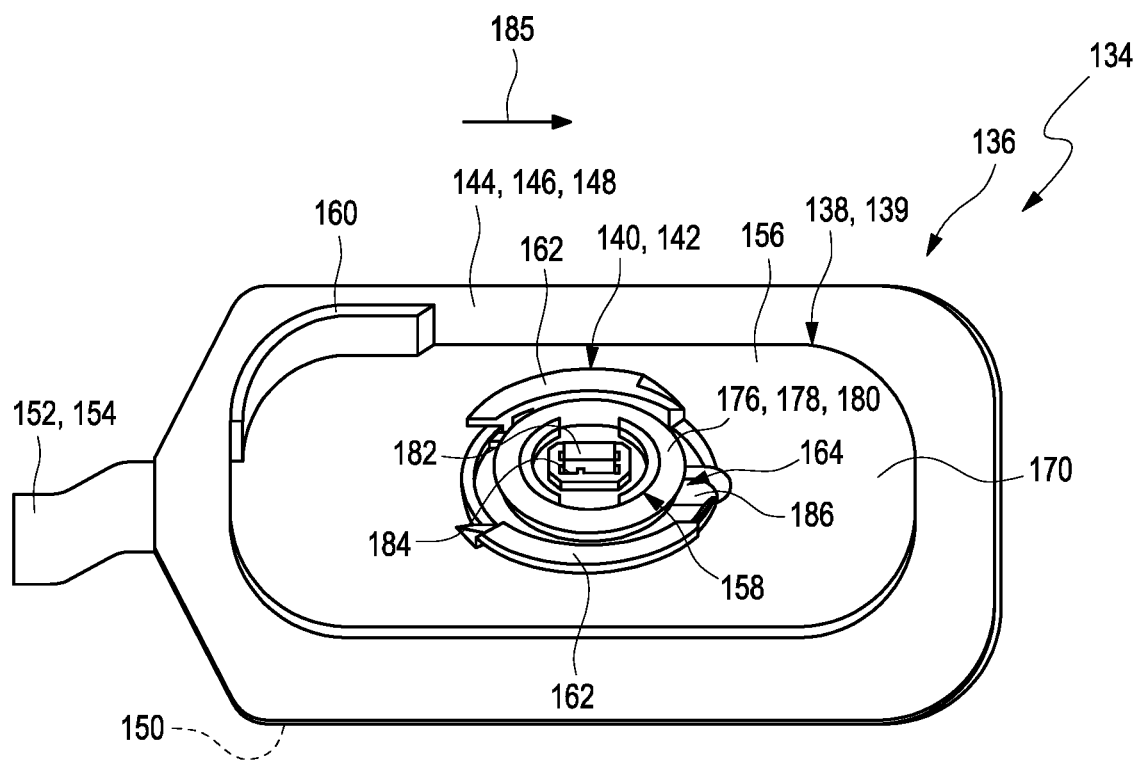
FIGS. 2A to 2C show an exemplary embodiment of a sensor patch (FIG. 2A) in a perspective view and in a sectional view (FIG. 2B) and of a connector element of the sensor patch in a perspective view (FIG. 2C) of a first embodiment of a sensor assembly.
Figure 2:
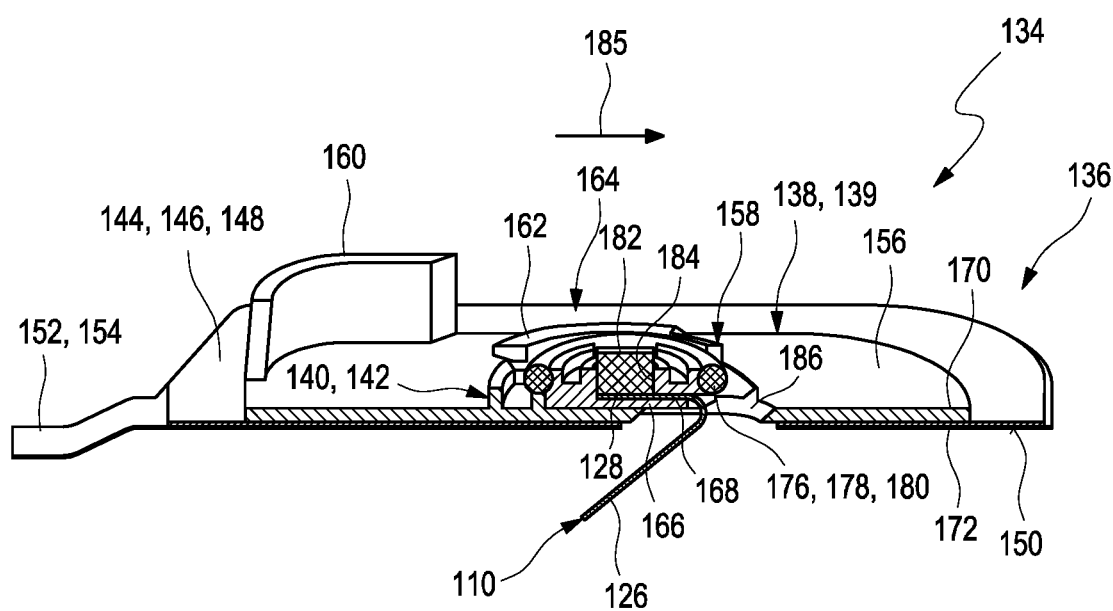
Figure 2:
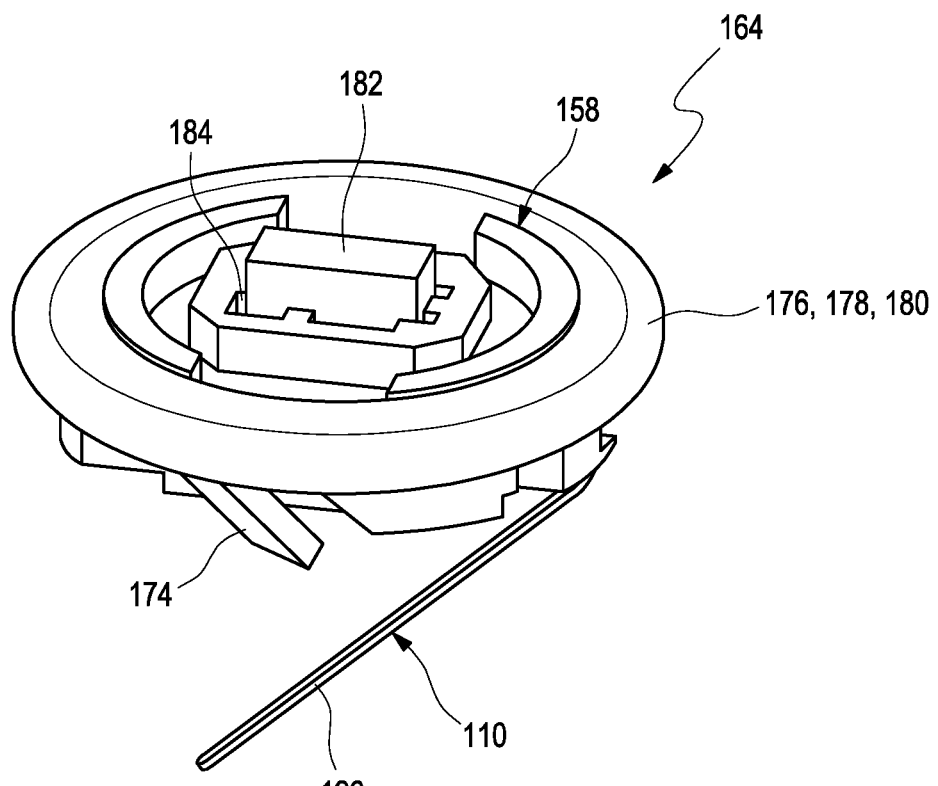

In the Figures, two embodiments of sensor assemblies 226 are shown in different configurations and in full or partial views. Therein, FIG. 1 shows a general example of a sensor 110 for detecting at least one analyte in a body fluid. FIGS. 2A-5B refer to a first exemplary embodiment of a sensor assembly 226, and FIGS. 6-10B refer to a second exemplary embodiment of a sensor assembly 226. As will be outlined in further detail below, the sensor assemblies 226 each comprise different components, such as a sensor patch 134, an electronics unit 188 and, optionally, an insertion device 240. Either the electronics unit 188 or the insertion device 240 may be coupled to the sensor patch 134 and/or to the body mount 136. Thus, for each of the two different embodiments, a first configuration with the electronics unit 188 coupled to the sensor patch 134 and/or the body mount 136 (see e.g. FIGS. 4A and 4B for the first embodiment or FIG. 9 for the second embodiment), and a second configuration with the insertion device 240 coupled to the sensor patch 134 and/or the body mount 136 (see e.g. FIGS. 5A and 5B for the first embodiment or FIGS. 10A and 10B for the second embodiment) may be defined. In the following, in the Figures in which the first configurations are shown, the respective electronics units 188, which also are part of the sensor assemblies 226, are not shown.

As outlined above, FIG. 1 shows an exemplary embodiment of a sensor 110 in a top view. The sensor 110 is configured for detecting at least one analyte in a body fluid.

The sensor 110 may preferably be an electrochemical sensor 112 configured to conduct an electrochemical measurement in order to detect the analyte. Exemplarily, an electrochemical detection reaction may be detected by comparing one or more electrode potentials. Therefore, the sensor 110 comprises at least two electrodes 114 configured for detecting the analyte and at least two sensor contacts 116 for electrically contacting the electrodes 114.

The electrodes 114 may comprise at least one working electrode 118 adapted for performing the electrochemical detection reaction. The working electrode 118 may have at least one test chemical being sensitive to the analyte to be detected. Further, the electrodes 114 may comprise at least one counter electrode 120 adapted for performing at least one electrochemical counter reaction, specifically for balancing a current flow required by the electrochemical detection reaction at the working electrode 118. Additionally, the electrodes 116 may further comprise at least one reference electrode 122 which may have a stable and well-known electrode potential. It shall be noted however, that other electrode setups may be feasible, such as setups having more than three electrodes 114 or less than three electrodes 114, such as by combining the counter electrode 120 and the reference electrode 122.

The electrodes 114 may be located on at least one substrate 124. The substrate 124 may be or may comprise a flexible substrate such as a flexible foil. Specifically, the substrate 124 may comprise at least one shaft 126 and at least one contact portion 128 whereas the contact portion 128 may be widened as compared to the remaining substrate 124. The electrodes 114 may be located at one end 130 of the substrate 124 opposing the contact portion 128 and the sensor contacts 116 may be located on the contact portion 128 of the substrate 124. The sensor 110 may further comprise electrical traces 132 which interconnect the sensor contacts 116 and the electrodes 114. The electrical traces 132 may have an elongate shape and may specifically be located on the shaft 126 of the substrate 124.

FIGS. 2A and 2B show an exemplary embodiment of a sensor patch 134 of the above-mentioned first embodiment of the sensor assembly 226 in a perspective view (FIG. 2A) and in a sectional view (FIG. 2B). FIG. 2C shows a connector element 164 of the sensor patch 134 (FIG. 2B) in a perspective view. The sensor patch 134 comprises the sensor 110 as illustrated in FIGS. 2B and 2C. The sensor 110 may correspond at least in wide parts to the sensor 110 as illustrated in FIG. 1. Thus, reference may be made to the description of FIG. 1 above. Still, other embodiments are feasible.

Further, the sensor patch 134 comprises at least one body mount 136 configured for attachment to a body of a user. Additionally, the sensor patch 134 comprises a patch housing 138 with a patch bayonet contour 140, preferably a patch bayonet screw 142. The patch housing 138 may also be referred to as base plate 139.

The body mount 136 may comprise at least one attachment component 144 capable of connecting the body mount 136 to the skin of the user. Exemplarily, the attachment component 144 may be at least one adhesive strip 146 or a plaster 148 and/or may comprise at least one adhesive surface 150. Further, the attachment component 144 may comprise at least one flexible extension 152 such as a flexible foil 154 configured to facilitate a handling of the sensor patch 134 for the user, specifically during attaching and detaching of the body mount 136 on the skin of the user.

The patch housing 138 may be formed by at least one body mount housing 156 of the body mount 136 and by a connector element housing 158 of the connector element 164. The body mount housing 156 may be used as a sensor support, for attachment of the sensor 110, such as the contact portion 128 of the sensor 110 as illustrated in FIG. 1. Optionally, the body mount housing 156 may comprise at least one finger rest 160. The finger rest 160 may provide an attachment of an electronics unit with only two fingers of the user and/or may be configured for guiding and/or holding an electronics unit as will further be described below.

The patch bayonet contour 140 may fully or partially be embodied within the body mount housing 156. The patch bayonet contour 140 may specifically comprise at least one protrusion 162 configured to interact with a counterpart bayonet contour as may further be described below in more detail.

The sensor 110 may specifically be attached to the body by the at least one connector element 164. The connector element 164 may comprise at least one base 166 to which the sensor 110 may partially be inserted as illustrated in FIG. 2B. Specifically, the contact portion 128 of the sensor 110 may be inserted into a first receptacle 168 of the connector element 164. Further, the connector element 164 may be connectable to the body mount 136, specifically on a front side 170 of the body mount housing 156 and the attachment component 144 may be located on a back side 172 of the body mount housing 156. Exemplarily, the connector element 164 may be connectable to the body mount 136 by a form-fit and/or a force-fit connection, preferably by at least one clip and/or by at least one snap fit connection. Thus, the connector element 164 may comprise one or more hooks 174 for forming the snap fit connection as illustrated in FIG. 2C. Optionally, the patch bayonet contour 140 as described above may partially be embodied within the connector element housing 158. Thus, as an example, the connector element 164 may comprise the patch bayonet contour 140 or at least parts thereof.

Further, at least one sealing element 176 may be part of the connector element 164. Specifically, the sealing element 176 may fully or partially be designed as a separate sealing element. The sealing element 176 may be integrated into the connector element 164 by multicomponent molding, preferably by multicomponent injection molding and/or by insert molding. Thus, the sealing element 176 may be or may comprise at least one compressible material, such as at least one flexible material. The sealing element 176 may specifically be or may comprise at least one sealing ring 178, specifically an O-ring 180.

Further, the connector element 164 may comprise at least one electrically conductive rubber material 182. The electrically conductive rubber material 182 may exemplarily have a cubic form. Further, the electrically conductive rubber material 182 may be located in a second receptacle 184 of the connector element 164. Specifically, the second receptacle 184 may be configured to suppress at least to a large extend a slide of the electrically conductive rubber material 182 along a direction of extension 185 of the sensor patch 134. The second receptacle 184 may be configured such that a direct connection, specifically an electrically conductive connection, between the electrically conductive rubber material 182 and the sensor 110 may be formed. Therefore, there may be an opening 186 between the first receptacle 168 and the second receptacle 184 as illustrated in FIG. 2B.

Moreover, the body mount housing 156 may comprise a through hole 186 which may extend from the front side 170 to the back side 172. The sensor 110 may extend at least partially through the through hole 186 in order to extend into a body tissue of the user. Specifically, the shaft 126 of the sensor 110 may extend at least partially through the through hole 186.

Figure 3:
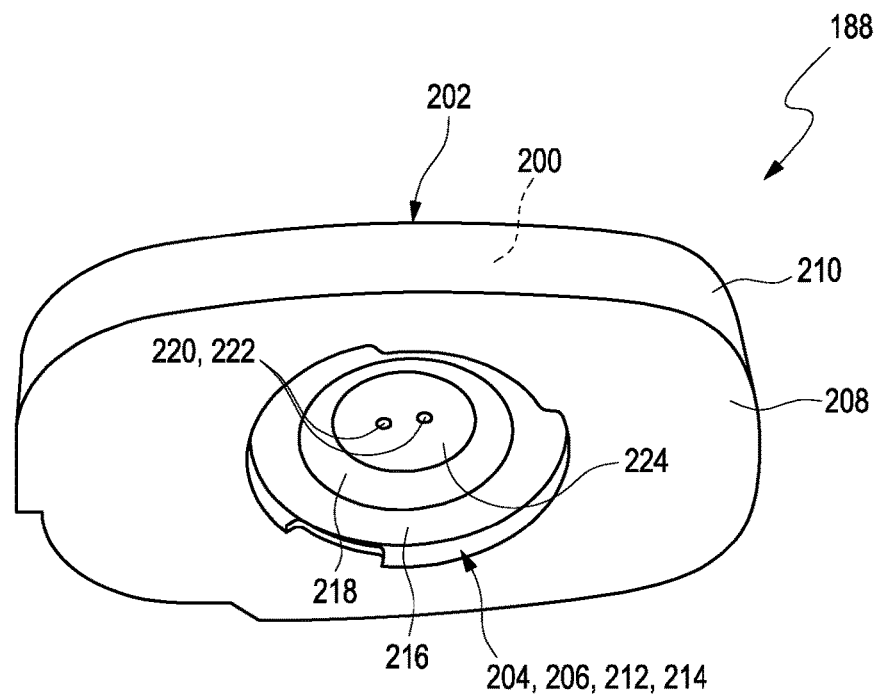
FIG. 3 shows an exemplary embodiment of an electronics unit of the first embodiment of the sensor assembly in a perspective view.
Figure 4:
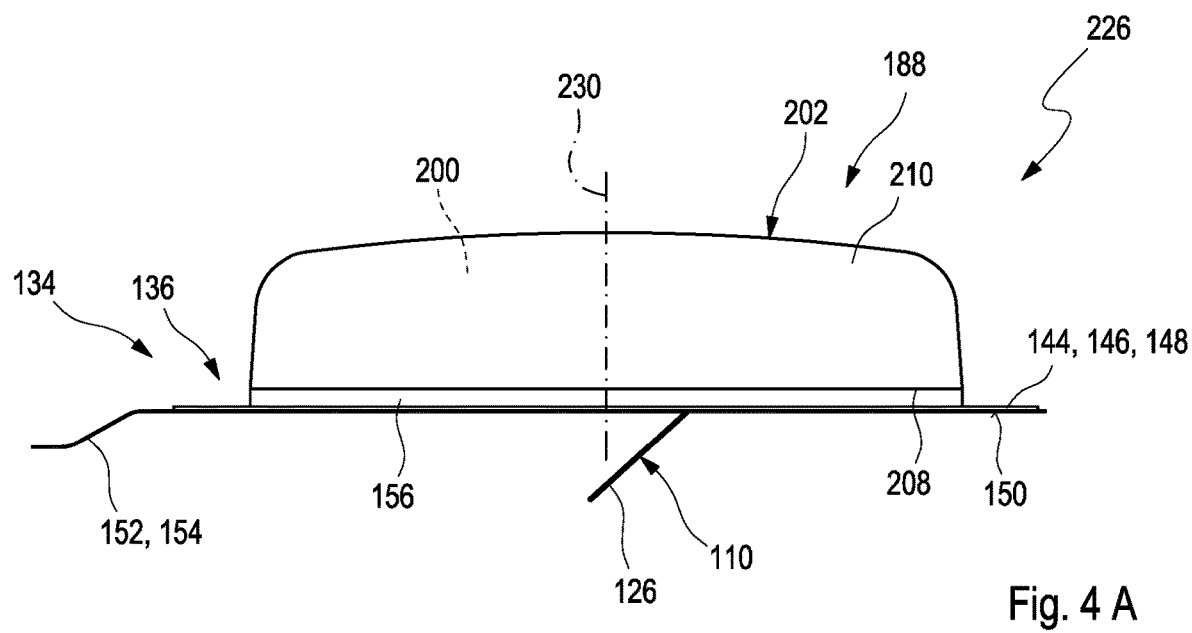
FIGS. 4A to 4B show the first exemplary embodiment of the sensor assembly in a perspective view (FIG. 4A) and in a sectional view (FIG. 4B), in an assembled state.
Figure 4:
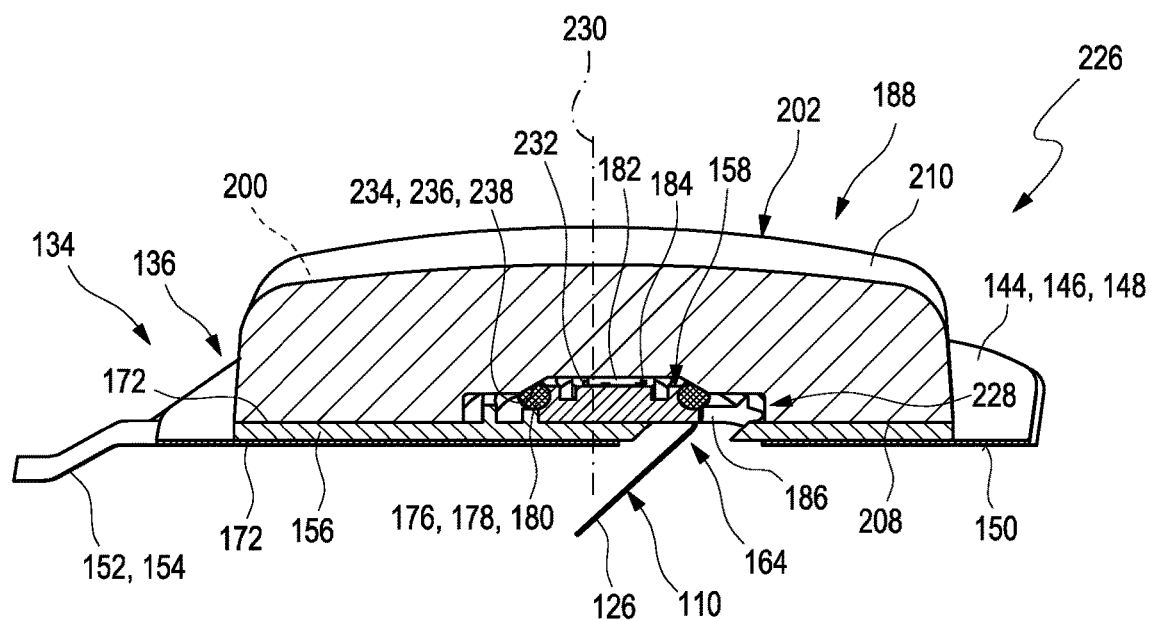

FIG. 3 shows an exemplary embodiment of an electronics unit 188 for use in the first embodiment of the sensor assembly 226 in a perspective view. Without limiting the possibility of alternative uses, the electronics unit 188 is often also referred to as a "re-usable", whereas the sensor patch 134 is also often referred to as the "disposable". The electronics unit 188 is attachable to the body mount 136 as described above. The electronics unit 188 has at least one electronics component 200 for one or more of controlling the detection of the analyte or transmitting measurement data to another component. Further, the electronics unit 188 comprises an electronics unit housing 202 having an electronics unit bayonet contour 204, preferably an electronics unit bayonet screw 206.

The electronics unit housing 202 may fully or partially surround the electronics components 200 of the electronics unit 188 and/or may hold one or more electronics components 200 of the electronics unit 188. Specifically, the electronics unit housing 202 may comprise one or more electronics unit housing base plates 208 and one or more electronics unit housing covers 210 which interact with the electronics unit housing base plate 208 in order to form an interior space configured for receiving the one or more electronics components 200 of the electronics unit 188.

The electronics unit bayonet contour 204 may be configured to interact with the patch bayonet contour 140 as described within FIGS. 2A to 2C. Thus, the electronics unit bayonet contour 204 may comprise at least one bayonet grove 212 or bayonet slot 214 in which the patch bayonet contour 140, specifically the protrusion 162 of the patch bayonet contour 140, such as described within FIGS. 2A to 2C may be guided. The electronics unit bayonet contour 204 may specifically comprise at least one first section 216 and at least one second section 218.

The electronics unit 188 further may comprise at least two electrical contacts 220 adapted for directly or indirectly contacting the sensor 110, such as the sensor 110 as illustrated in FIG. 1, exemplarily via the sensor contacts 116 of the sensor 110. As an example, the electrical contacts 220 of the electronics unit 188 may be or may comprise two or more contact pads 222. The electrical contacts 220 of the electronics unit 188 may be located on a lower side 224 of the electronics unit 188. Specifically, the lower side 224 may be located within the second section 218 of the electronics unit bayonet contour 204.

As outlined above, FIGS. 4A to 4B show an exemplary embodiment of a first embodiment of a sensor assembly 226 in a perspective view (FIG. 4A) and in a sectional view (FIG. 4B), in a first configuration with the electronics unit 188 attached to the body mount 136 and/or attached to the sensor patch 134. The sensor assembly 226 comprises the sensor patch 134 having the body mount 136 and the sensor 110 and the electronics unit 188. The sensor patch 134 and the electronics unit 188 correspond at least in large parts to the sensor patch 134 and the electronics unit 188 as described within FIGS. 2A to 2C and FIG. 3, respectively. Thus, reference can be made to the descriptions of FIGS. 2A to 2C and FIG. 3 above.

FIGS. 4A and 4B show the sensor assembly 226 in an assembled state. The patch bayonet contour 140 of the sensor patch 134 and the electronics unit bayonet contour 204 in conjunction form a bayonet connector 228 configured for establishing a releasable mechanical connection between the electronics unit 188 and the sensor patch 134.

In a mated state, in which the releasable mechanical connection between the electronics unit 188 and the sensor patch 134 may be established by the bayonet connector 228, an electrical connection between the sensor contacts 116 and the electrical contacts 220 of the electronics unit 188 may be established. Thereby, the electronics unit 188 may specifically be pressed onto the sensor patch 134 or vice versa by means of the bayonet connector 228. The bayonet connector 228 may at least partially surround the electrical connection between the sensor contacts 116 and the electrical contacts 220 of the electronics unit 188.

In the first section 216 of the electronics unit bayonet contour 214, the protrusion 162 of the may simply be moved in an essentially axial fashion, such as at an angle of no more than 20°, e.g. no more than 10°, no more than 5° or even 0° with respect to an axis 230 which interconnects the electronics unit bayonet contour 214 and the patch bayonet contour 140.

Thus, as an example, while the protrusion 162 of the patch bayonet contour 140 is guided in the first section 216, the electronics unit bayonet contour 214 and the patch bayonet contour 140 simply may be pushed together along the axis 230. In the second section 218 the protrusion 162 may be guided in a spiral or screw-like fashion around the axis 230.

The sealing element 176 may specifically be configured for sealing off at least one region 232 in between the sensor patch 134 and the electronics unit 188 when the releasable mechanical connection between the electronics unit 188 and the sensor patch 134 is established. Specifically, the bayonet connector 228 may be configured to self-center the sealing element 176 when the releasable mechanical connection is formed. The bayonet connector 228 may comprise at least one angled surface 234, preferably at least one conical surface 236. When the releasable mechanical connection may be formed, the sealing element 176 may be pressed onto the angled surface 236. The angled surface 236 may form a sealing contour 238.

FIGS. 5A to 5B show the first embodiment of the sensor assembly 226 in a cross-sectional view, in a second configuration with the electronics unit 188 removed from the body mount 136 and replaced by an insertion device 240. The sensor assembly 226 comprises the sensor patch 134 having the body mount 136 and the sensor 110. The sensor patch 134 corresponds at least in wide parts to the sensor patch 134 as depicted in FIGS. 4A to 4B. Thus, reference may be made to the description of FIGS. 4A and 4B above.

The sensor assembly 226 may further comprise at least one insertion device 240. The insertion device 240 may be configured for at least partially inserting the sensor 110 into the body tissue of the user. The insertion device 240 may be configured to be mountable to the body mount 136. Thus, the insertion device 240 may comprise at least one insertion device housing 242 having an insertion device bayonet contour 244. The insertion device bayonet contour 244 may be configured for establishing a releasable mechanical connection between the insertion device 240 and the sensor patch 134. The insertion device bayonet contour 244 may correspond at least in wide parts to the electronics unit bayonet contour 204 as illustrated in FIG. 3. Thus, reference can be made to the description of FIG. 3 above.

The insertion device 240 may comprise at least one slide 246. The slide 246 may be configured to hold the connector element 164 with the sensor 110 attached thereto and to connect the connector element 164 to the body mount 136. The slide 264 may comprise a releasable connector 248 for engaging the connector element 164, in order to hold the connector element 164 before the connector element 164 is connected to the body mount 136. The slide 246 may be configured to be guidable in a slidable fashion in such a way that the slide 246 moves toward the body mount 136 and transfers the connector element 164. Thereafter, the slide 246 may be configured to release the connector element 164 in order to move back from the body mount 136 with the connector element 164 and the sensor 110 remaining attached to the body mount 136. For moving the slide 246, the insertion device 240 may comprise at least one lever 250 as illustrated in FIG. 5A for actuation by the user and for inserting the sensor 110 into the body tissue. The insertion device 240 may further comprise at least one insertion cannula 252 attached to the slide 246. The sensor 110 may be receivable in the insertion cannula 252 when the connector element 164 is held by the slide 246.

Figure 5:
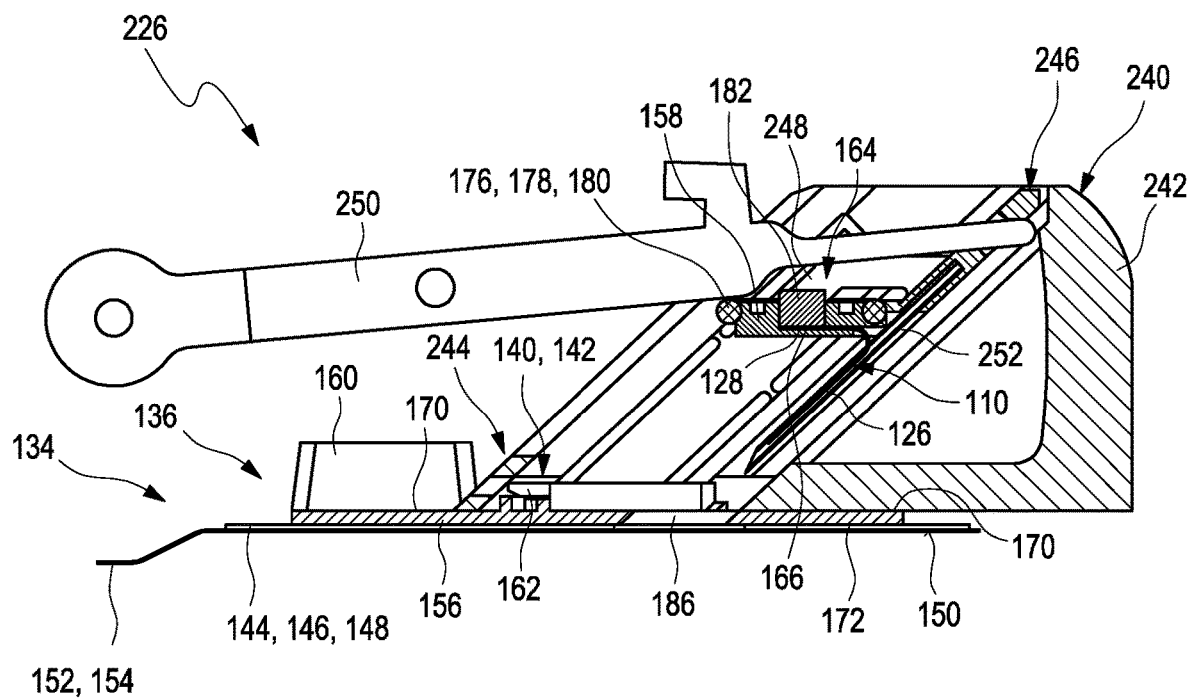
FIGS. 5A to 5B show an alternative configuration of the first exemplary embodiment of the sensor assembly in a cross-sectional view, with the electronics unit replaced by an insertion device.
Figures 5, 6:
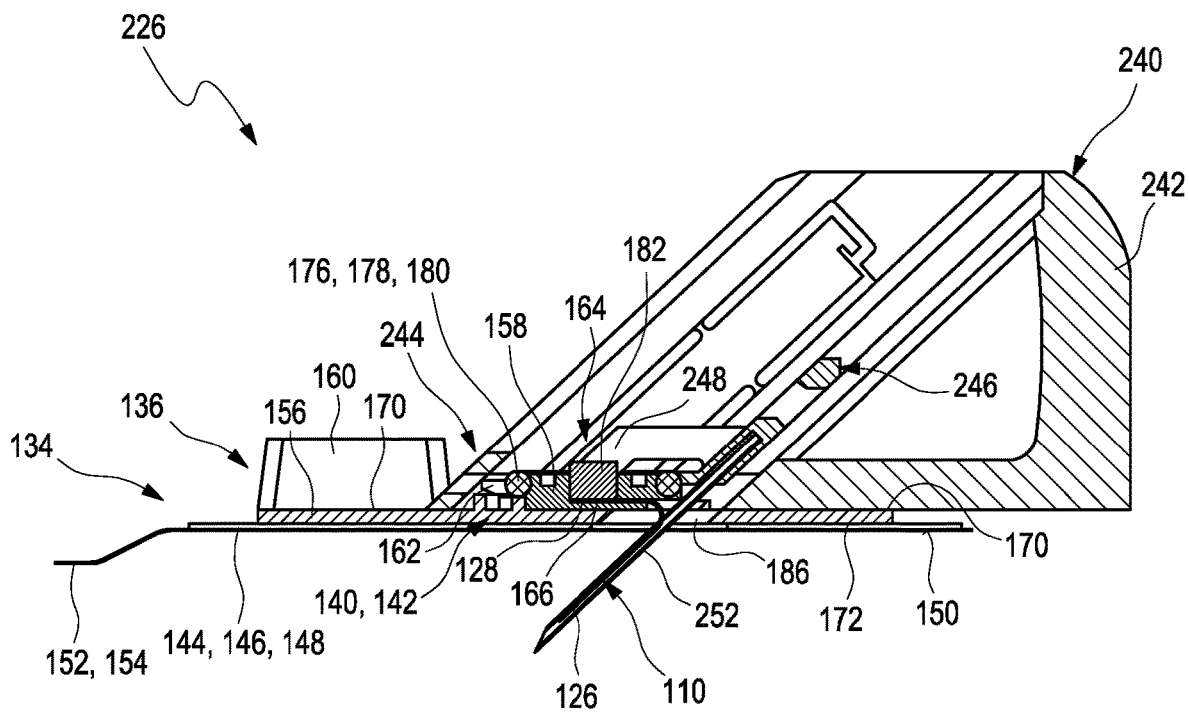
FIG. 6 shows a further exemplary embodiment of an electronics unit of a second exemplary embodiment of a sensor assembly, in a perspective view.

FIG. 6 shows an exemplary embodiment of the electronics unit 188 of the second embodiment of the sensor assembly 226 in a perspective view. The electronics unit 188 may correspond in wide parts to the electronics unit 188 as depicted in FIG. 3. Thus, reference may be made to the description of FIG. 3 above.

The electronics unit 188 as depicted in FIG. 6 differs from the electronics unit 188 as described in FIG. 3 by an embodiment of the electronics unit bayonet contour 204.

The electronics unit bayonet contour 204 as depicted in FIG. 6 may comprise at least one electronics unit bayonet contour protrusion 254. The electronics unit bayonet contour protrusion 254 may have a cylindrical shape. An electronics unit bayonet contour receptacle 256 may be located within the electronics unit bayonet contour protrusion 254. The electronics unit bayonet contour receptacle 256 may have a round cross-section and may have a smaller diameter than the electronics unit bayonet contour protrusion 254. The electrical contacts 22 may be located on a surface 258 of the electronics unit bayonet contour receptacle 258.

FIG. 7 shows an exemplary embodiment of the sensor patch 134 of the second embodiment of the sensor assembly 226 in a perspective view. The sensor patch 134 corresponds in wide parts to the sensor patch 134 as depicted in FIGS. 2A and 2B. Thus, reference may be made to the description of FIGS. 2A and 2B above.

The sensor patch 134 as depicted in FIG. 7 differs from the sensor patch 134 as described in FIGS. 2A and 2B by an embodiment of the patch bayonet contour 140. The patch bayonet contour 140 as illustrated in FIG. 7 may comprise at least one patch bayonet contour receptacle 260 configured for receiving the electronics unit bayonet contour protrusion 254 as illustrated in FIG. 6. Thus, the patch bayonet contour receptacle 260 may comprise a round cross-section. Moreover, the patch bayonet contour receptacle 260 may comprise a further receptacle 262 configured for receiving the connector element 164.

FIGS. 8A and 8B show an embodiment of the connector element 164 in an assembled state (FIG. 8A) and in a disassembled state (FIG. 8B). The connector element 164 is shown in a cross-sectional view in FIG. 8A and in a perspective view in FIG. 8B. The connector element 164 may be configured to be receivable in the sensor patch 134 as depicted in FIG. 7. Further, the connector element 164 as illustrated in FIGS. 8A and 8B may correspond at least partially to the connector element 164 as depicted in FIG. 2C. Thus, reference can be made to the description of FIG. 2C above.

The connector element 164 as illustrated in FIGS. 8A and 8B may comprise at least one flexible printed circuit (FPC) connector 264. The flexible printed circuit (FPC) connector 264 may be embodied as a separate conductive element. The sensor 110, specifically the contact portion 128 of the sensor 110, may be connected to the flexible printed circuit (FPC) connector 264, such as plugged into the flexible printed circuit (FPC) connector 264. Further, circuit board 266 may be connected to the flexible printed circuit (FPC) connector 264 configured to contact the electrical contacts 220 of the electronics unit 188 as illustrated in FIG. 6. Therefore, the circuit board 266 may comprise at least two, specifically three, spring contacts 268. The spring contacts 268 may comprise at least one supporting surface 270 configured to attach to the electrical contacts 220 of the electronics unit 188. Thus, the connector element housing 158 may comprise passage openings 272, specifically one passage opening 172 for each spring contact 268, respectively.

Figure 9:
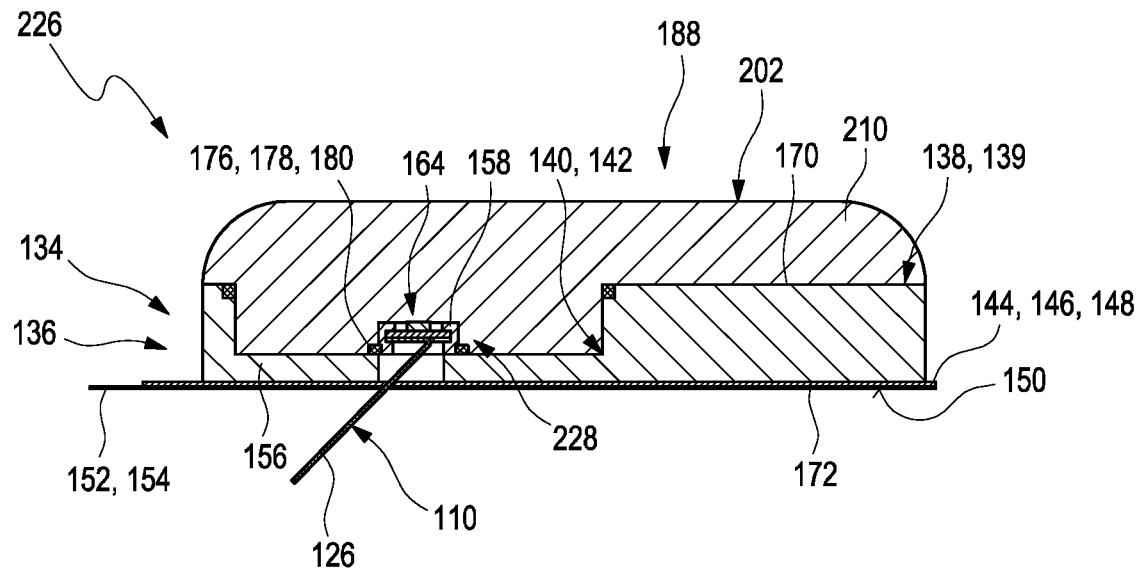
FIG. 9 shows the second exemplary embodiment of the sensor assembly in a cross-sectional view, in an assembled state.
Figure 10:
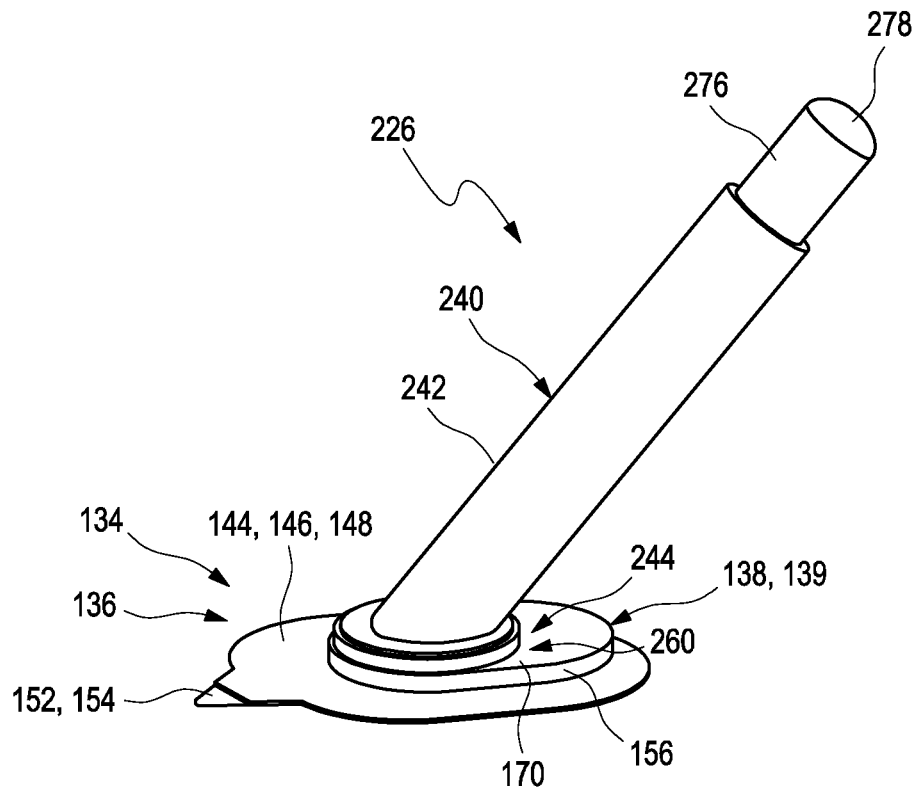
FIGS. 10A and 10B show an alternative configuration of the second exemplary embodiment of the sensor assembly in a perspective view (FIG. 10A) and in a cross-sectional view (FIG. 10B), with the electronics unit replaced by an insertion device.
Figure 10:
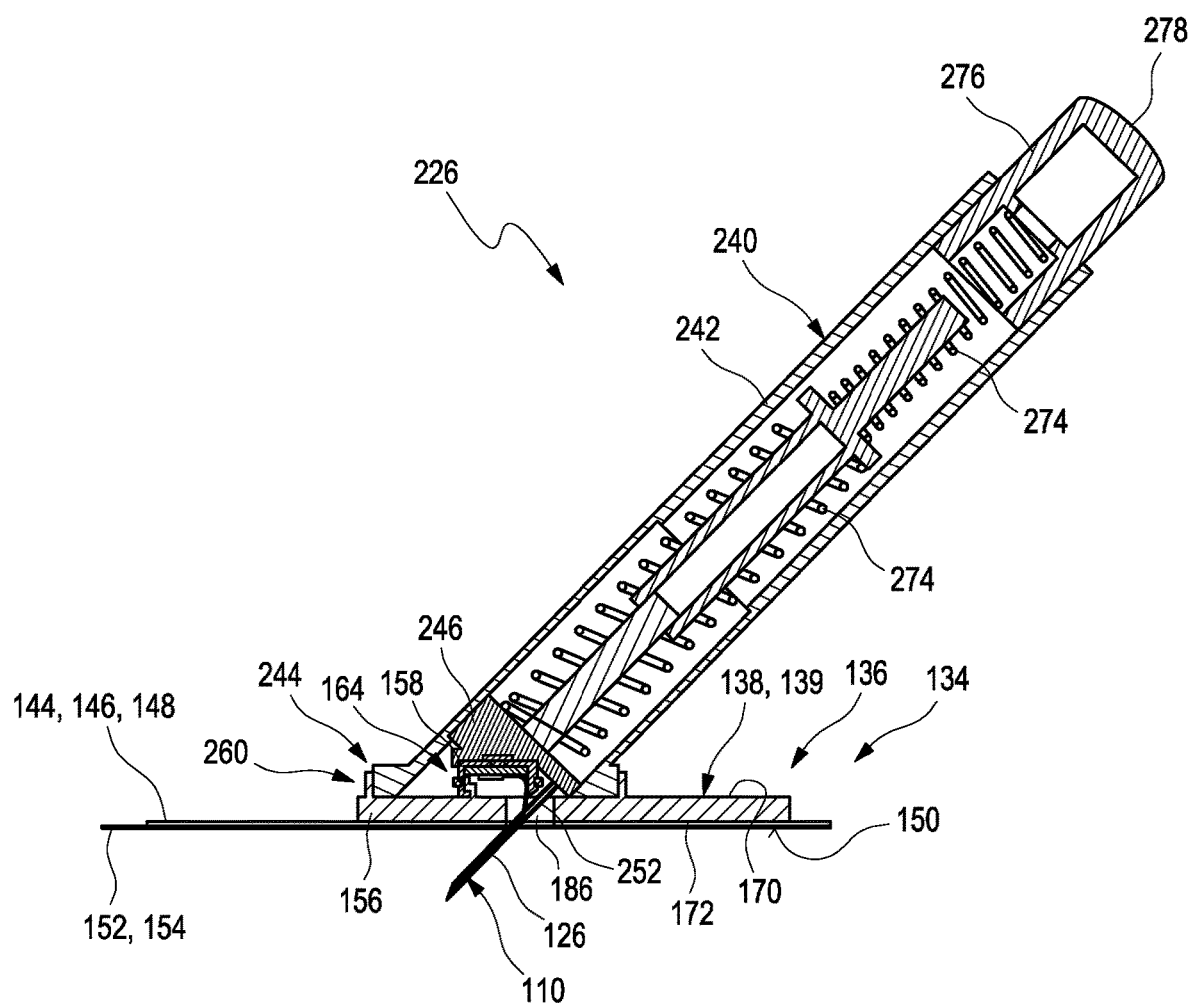

FIG. 9 shows the second exemplary embodiment of the sensor assembly 226 in an assembled state, with the electronics unit 188 coupled to the sensor patch 134 and/or to the body mount 136, i.e. in the above-defined first configuration, in a cross-sectional view. The sensor assembly comprises the electronics unit 188 and the sensor patch 134. The electronics unit 188 and the sensor patch 134 correspond to the electronics unit 188 and the sensor patch 134 as illustrated in FIG. 6 and FIG. 7, respectively. Thus, reference can be made to the description of FIGS. 6 and 7 above.

The flexible printed circuit connector 264 may be configured to electrically contact the electronics unit 188 once a mechanical connection by using the bayonet connector 228 is established. Thereby, the flexible printed circuit (FPC) connector 264 may fully or partially be surrounded by the bayonet connector 228.

FIGS. 10A and 10B show the second exemplary embodiment of the sensor assembly 226 in the above-defined second configuration, i.e. with the electronics unit 188 removed from the sensor patch 134 and/or from the body mount 136 and replaced by an insertion device 240, in a perspective view (FIG. 10A) and in a cross-sectional view (FIG. 10B). Again, the electronics unit 188 is not shown in these Figures, as in FIGS. 5A and 5B. The sensor assembly 226 comprises the sensor patch 134 having the body mount 136 and the sensor 110. The sensor patch 134 corresponds at least in wide parts to the sensor patch 134 as depicted in FIG. 7. Thus, reference can be made to the description of FIG. 7 above.

The sensor assembly 226 may further comprise the insertion device 240. The insertion device 240 may be configured for at least partially inserting the sensor 110 into the body tissue of the user. Thus, the insertion device 240 may comprise the insertion device housing 242 having an insertion device bayonet contour 244. The insertion device bayonet contour 244 may be configured for establishing a releasable mechanical connection between the insertion device 240 and the sensor patch 134. The insertion device bayonet contour 244 may correspond at least in wide parts to the electronics unit bayonet contour 204 as illustrated in FIG. 6. Thus, reference can be made to the description of FIG. 6 above.

The insertion device 240 may comprise the slide 246. The slide 246 may be configured to hold the connector element 164 with the sensor attached thereto and to connect the connector element 164 to the body mount 136. The insertion device 240 may at least partially correspond to the insertion device 240 as illustrated in FIGS. 5A and 5B. Thus, reference can be made to the description of FIGS. 5A and 5B above. However, the insertion device 240 as illustrated in FIGS. 10A and 10B may comprise a spring element 274 which is configured to move the slide 246. Specifically, the insertion device 240 may be configured to be handled manually by the user. The insertion device 240 may comprise at least one button 276 located at one end 278 of the insertion device 240 opposing the insertion device bayonet contour 244. The button 276 may be configured to pull the connector element 164 towards the body mount 136 via the spring element 274.

LIST OF REFERENCE NUMBERS 110 sensor
112 electrochemical sensor
114 electrodes
116 sensor contacts
118 working electrode
120 counter electrode
122 reference electrode
124 substrate
126 shaft
128 contact portion
130 end
132 electrical traces
134 sensor patch
136 body mount
138 patch housing 139 base plate
140 patch bayonet contour
142 patch bayonet screw
144 attachment component
146 adhesive strip
148 plaster
150 adhesive surface
152 flexible extension
154 flexible foil
156 body mount housing
158 connector element housing
160 finger rest
162 protrusion
164 connector element
166 base
168 first receptacle
170 front side
172 back side
174 hock
176 sealing element
178 sealing ring
180 O-ring
182 electrically conductive rubber material
184 second receptacle
185 direction of extension
186 through hole
188 electronics unit
200 electronics component
202 electronics unit housing
204 electronics unit bayonet contour
206 electronics unit bayonet screw
208 electronics unit housing base plate
210 electronics unit housing covers
212 bayonet grove
214 bayonet slot
216 first section
218 second section
220 electrical contact
222 contact pad
224 lower side
226 sensor assembly
228 bayonet connector
230 axis
232 region
234 angled surface
236 conical surface
238 sealing contour
240 insertion device
242 insertion device housing
244 insertion device bayonet contour
246 slide
248 releasable connector
250 lever
252 insertion cannula
254 electronics unit bayonet contour protrusion
256 electronics unit bayonet contour receptacle
258 surface
260 patch bayonet contour receptacle
262 further receptacle
264 flexible printed circuit connector
266 circuit board
268 spring contact
270 supporting surface
272 passage openings
274 spring element
276 button
278 end

The invention claimed is:

1. A sensor assembly for detecting at least one analyte in a body fluid, comprising:
at least one sensor patch, having
at least one body mount configured for attachment to a body of a user; and
at least one sensor for detecting the at least one analyte in the body fluid, the at least one sensor having at least two electrodes configured for detecting the at least one analyte, the at least one sensor further having at least two sensor contacts for electrically contacting the at least two electrodes, the at least one sensor being a transcutaneous sensor;
wherein the at least one sensor patch comprises a patch housing with a patch bayonet contour;
at least one electronics unit attachable to the at least one body mount, having at least one electronics component for one or more of controlling the detection of the at least one analyte or transmitting measurement data to another component,
wherein the at least one electronics unit further comprises an electronics unit housing having an electronics unit bayonet contour;
wherein the patch bayonet contour and the electronics unit bayonet contour in conjunction form a bayonet connector configured for establishing a releasable mechanical connection between the at least one electronics unit and the at least one sensor patch,
wherein the at least one electronics unit further comprises at least two electrical contacts, wherein mating the at least one electronics unit with the at least one sensor patch to form the releasable mechanical connection between the at least one electronics unit and the at least one sensor patch by the bayonet contours provides an electrical connection between the at least two sensor contacts of the at least one sensor and the at least two electrical contacts of the at least one electronics unit, and
the sensor assembly further comprising at least one sealing element sealing the electrical connection between the at least two sensor contacts of the at least one sensor and the at least two electrical contacts of the at least one electronics unit from a surrounding environment upon forming the releasable mechanical connection between the at least one electronics unit with the at least one sensor patch using the bayonet contours, in which the at least one sealing element is part of at least one of the patch bayonet contour and the electronics unit bayonet contour.

2. The sensor assembly according to claim 1, wherein in a mated state, the bayonet connector at least partially surrounds the electrical connection between the at least two sensor contacts of the at least one sensor and the at least two electrical contacts of the at least one electronics unit.

3. The sensor assembly according to claim 1, wherein the electrical connection between the at least two sensor contacts of the at least one sensor and the at least two electrical contacts of the at least one electronics unit is established by at least one of: an electrically conductive rubber material; an anisotropic electrically conductive rubber material; a Zebra connector; an electrically conductive spring contact; a flexible printed circuit connector; and a contact pin.

4. The sensor assembly according to claim 1, further including a flexible printed circuit connector, wherein the at least one sensor is plugged into the flexible printed circuit connector, wherein a second electrical connection is directly or indirectly established between the flexible printed circuit connector and the at least one electronics unit.

5. The sensor assembly according to claim 4, further including an at least one circuit board, wherein the second electrical connection is indirectly established between the flexible printed circuit connector and the at least one electronics unit via the at least one circuit board.

6. The sensor assembly according to claim 1, wherein in a mated state, in which the releasable mechanical connection between the at least one electronics unit and the at least one sensor patch is established by the bayonet connector, the at least one electronics unit is pressed onto the at least one sensor patch or vice versa, by means of the bayonet connector.

7. The sensor assembly according to claim 1, wherein the bayonet connector is configured to self-center the at least one sealing element when the releasable mechanical connection is formed.

8. The sensor assembly according to claim 7, wherein the bayonet connector comprises at least one angled surface, wherein, when the releasable mechanical connection is formed, the at least one sealing element is pressed onto the at least one angled surface.

9. The sensor assembly according to claim 1, wherein the at least one sensor is attached to at least one connector element, wherein the at least one connector element is connectable to the at least one body mount.

10. The sensor assembly according to claim 9, the sensor assembly further comprising at least one slide, wherein the at least one slide is configured to hold the at least one connector element with the at least one sensor attached thereto and to connect the at least one connector element to the at least one body mount.

11. The sensor assembly according to claim 10, wherein the sensor assembly further comprises at least one insertion device for at least partially inserting the at least one sensor into a body tissue of the user, wherein the at least one slide is part of the at least one insertion device and wherein the at least one insertion device is configured for moving the at least one slide towards the at least one body mount during insertion.

12. The sensor assembly of claim 1 in which the at least one electronics unit has a first position against the at least one sensor patch, and a second position rotated and engaging the bayonet connector.

13. The sensor assembly of claim 1 in which the at least one sealing element is pressed against an angled surface of the bayonet connector.

14. The sensor assembly of claim 1 in which the at least one sealing element presses against an angled surface of the other of the at least one patch bayonet contour and the at least one electronics unit bayonet contour.

15. A sensor patch for use in a sensor assembly comprising:
at least one body mount configured for attachment to a body of a user;
at least one sensor for detecting at least one analyte in a body fluid, the at least one sensor having at least two electrodes configured for detecting the at least one analyte, the at least one sensor further having at least two sensor contacts for electrically contacting the at least two electrodes, the at least one sensor being a transcutaneous sensor, and
a patch housing with a patch bayonet contour for establishing a releasable mechanical connection between at least one electronics unit and the sensor patch, wherein the patch housing further comprises at least one sealing element sealing an electrical connection between the at least two sensor contacts of the at least one sensor and at least two electrical contacts of the at least one electronics unit from a surrounding environment upon forming the releasable mechanical connection between the at least one electronics unit with the sensor patch using the patch bayonet contour, in which the at least one sealing element is part of the patch bayonet contour.

16. An electronics unit for use in a sensor assembly comprising:
at least one electronics component for one or more of controlling detection of the analyte or transmitting measurement data to another component,
wherein the at least one electronics component further comprises an electronics unit housing having an electronics unit bayonet contour for establishing a releasable mechanical connection between the electronics unit and a sensor patch,
wherein the electronics unit further comprises at least two electrical contacts, wherein, in a mated state, in which the releasable mechanical connection between the electronics unit and the sensor patch is established by the electronics unit bayonet contour, an electrical connection between at least two electrical contacts of the sensor patch and the at least two electrical contacts of the electronics unit, and
wherein the electronic unit housing further comprises at least one sealing element sealing the electrical connection between the at least two sensor contacts of the sensor patch and the at least two electrical contacts of the electronics unit from a surrounding environment upon forming the releasable mechanical connection between the electronics unit and the sensor patch using the electronics unit bayonet contour, in which the at least one sealing element is part of the electronics unit bayonet contour.

17. A method for producing a sensor assembly for detecting at least one analyte in a body fluid, the method comprising:
providing at least one sensor patch, having at least one body mount configured for attachment to a body of a user; and at least one sensor for detecting the at least one analyte in the body fluid,
the at least one sensor having at least two electrodes configured for detecting the at least one analyte, the at least one sensor further having at least two sensor contacts for electrically contacting the at least two electrodes, and
the at least one sensor being a transcutaneous sensor; wherein the at least one sensor patch comprises a patch housing with a patch bayonet contour;
providing at least one electronics unit attachable to the at least one body mount, the at least one electronics unit having at least one electronics component for one or more of controlling the detection of the at least one analyte or transmitting measurement data to another component,
wherein the at least one electronics unit further comprises an electronics unit housing having an electronics unit bayonet contour;
establishing a releasable mechanical connection between the at least one electronics unit and the at least one sensor patch by using a bayonet connector formed by the patch bayonet contour and the electronics unit bayonet contour forming the sensor assembly, the at least one electronics unit further comprising at least two electrical contacts, wherein, in a mated state, in which the releasable mechanical connection between the at least one electronics unit and the at least one sensor patch is established by the bayonet connector, an electrical connection between the at least two sensor contacts of the at least one sensor and the at least two electrical contacts of the at least one electronics unit, wherein the sensor assembly further comprises at least one sealing element sealing the electrical connection between the at least two sensor contacts of the at least one sensor and the at least two electrical contacts of the at least one electronics unit from a surrounding environment upon forming the releasable mechanical connection between the at least one electronics unit and the at least one sensor patch using the bayonet contours, in which the at least one sealing element is part of at least one of the patch bayonet contour and the electronics unit bayonet contour.

* * * * *